US008048448B2

(12) United States Patent
Ludwig et al.

(10) Patent No.: US 8,048,448 B2
(45) Date of Patent: Nov. 1, 2011

(54) NANOSHELLS FOR DRUG DELIVERY

(75) Inventors: Florian N. Ludwig, Mountain View, CA (US); Stephen D. Pacetti, San Jose, CA (US); Syed F. A. Hossainy, Fremont, CA (US); Dariush Davalian, San Jose, CA (US)

(73) Assignee: Abbott Cardiovascular Systems Inc., Santa Clara, CA (US)

( * ) Notice: Subject to any disclaimer, the term of this patent is extended or adjusted under 35 U.S.C. 154(b) by 1439 days.

(21) Appl. No.: 11/454,813

(22) Filed: Jun. 15, 2006

(65) Prior Publication Data
US 2007/0292495 A1    Dec. 20, 2007

(51) Int. Cl.
A61K 9/127    (2006.01)
A61K 9/14     (2006.01)

(52) U.S. Cl. .......................... 424/450; 424/489

(58) Field of Classification Search .................. None
See application file for complete search history.

(56) References Cited

U.S. PATENT DOCUMENTS

| | | | |
|---|---|---|---|
| 2,072,303 A | 3/1937 | Herrmann et al. |
| 2,386,454 A | 10/1945 | Frosch et al. |
| 2,647,017 A | 7/1953 | Coulliette |
| 2,701,559 A | 2/1955 | Cooper |
| 3,288,728 A | 11/1966 | Gorham |
| 3,687,135 A | 8/1972 | Stroganov et al. |
| 3,773,737 A | 11/1973 | Goodman et al. |
| 3,839,743 A | 10/1974 | Schwarcz |
| 3,849,514 A | 11/1974 | Gray, Jr. et al. |
| 3,900,632 A | 8/1975 | Robinson |
| 4,075,045 A | 2/1978 | Rideout |
| 4,104,410 A | 8/1978 | Malecki |
| 4,110,497 A | 8/1978 | Hoel |
| 4,132,357 A | 1/1979 | Blackinton |
| 4,164,524 A | 8/1979 | Ward et al. |
| 4,226,243 A | 10/1980 | Shalaby et al. |
| 4,321,711 A | 3/1982 | Mano |
| 4,323,071 A | 4/1982 | Simpson et al. |
| 4,329,383 A | 5/1982 | Joh |
| 4,338,942 A | 7/1982 | Fogarty |
| 4,343,931 A | 8/1982 | Barrows |
| 4,346,028 A | 8/1982 | Griffith |
| 4,439,185 A | 3/1984 | Lundquist |
| 4,489,670 A | 12/1984 | Mosser et al. |
| 4,516,972 A | 5/1985 | Samson et al. |
| 4,529,792 A | 7/1985 | Barrows |
| 4,538,622 A | 9/1985 | Samson et al. |
| 4,554,929 A | 11/1985 | Samson et al. |
| 4,573,470 A | 3/1986 | Samson et al. |
| 4,596,574 A | 6/1986 | Urist |
| 4,599,085 A | 7/1986 | Riess et al. |
| 4,608,984 A | 9/1986 | Fogarty |
| 4,611,051 A | 9/1986 | Hayes et al. |
| 4,612,009 A | 9/1986 | Drobnik et al. |
| 4,616,593 A | 10/1986 | Kawamura et al. |
| 4,616,652 A | 10/1986 | Simpson |
| 4,629,563 A | 12/1986 | Wrasidlo |
| 4,633,873 A | 1/1987 | Dumican et al. |
| 4,638,805 A | 1/1987 | Powell |
| 4,656,083 A | 4/1987 | Hoffman et al. |
| 4,656,242 A | 4/1987 | Swan et al. |
| 4,699,611 A | 10/1987 | Bowden |
| 4,702,252 A | 10/1987 | Brooks et al. |
| 4,718,907 A | 1/1988 | Karwoski et al. |
| 4,722,335 A | 2/1988 | Vilasi |
| 4,723,549 A | 2/1988 | Wholey et al. |
| 4,732,152 A | 3/1988 | Wallstén et al. |
| 4,733,665 A | 3/1988 | Palmaz |
| 4,739,762 A | 4/1988 | Palmaz |
| 4,740,207 A | 4/1988 | Kreamer |
| 4,743,252 A | 5/1988 | Martin, Jr. et al. |
| 4,748,982 A | 6/1988 | Horzewski et al. |
| 4,768,507 A | 9/1988 | Fischell et al. |
| 4,774,039 A | 9/1988 | Wrasidlo |
| 4,776,337 A | 10/1988 | Palmaz |
| 4,800,882 A | 1/1989 | Gianturco |
| 4,816,339 A | 3/1989 | Tu et al. |
| 4,818,559 A | 4/1989 | Hama et al. |
| 4,828,561 A | 5/1989 | Woodroof |
| 4,850,999 A | 7/1989 | Planck |
| 4,865,870 A | 9/1989 | Hu et al. |
| 4,871,542 A | 10/1989 | Vilhardt |
| 4,877,030 A | 10/1989 | Beck et al. |
| 4,878,906 A | 11/1989 | Lindemann et al. |
| 4,879,135 A | 11/1989 | Greco et al. |
| 4,880,683 A | 11/1989 | Stow |

(Continued)

FOREIGN PATENT DOCUMENTS

CA    2 008 312    7/1990

(Continued)

OTHER PUBLICATIONS

PM Kasili, T Vo-Dinh. "Photothermal Treatment of Human Carcinoma Cells Using Liposome-Encapsulated Gold Nanoshells." NanoBiotechnology, vol. 1 No. 3, Sep. 2005, p. 245-252.*

(Continued)

*Primary Examiner* — Frederick Krass
*Assistant Examiner* — Isaac Shomer
(74) *Attorney, Agent, or Firm* — Squire, Sanders & Dempsey (US) LLP; Randy Shen, Esq.

(57) ABSTRACT

Nano-constructs comprising nanoshells and methods of using the nano-constructs for treating or ameliorating a medical condition are provided.

28 Claims, No Drawings

U.S. PATENT DOCUMENTS

| | | | |
|---|---|---|---|
| 4,882,168 A | 11/1989 | Casey et al. | |
| 4,886,062 A | 12/1989 | Wiktor | |
| 4,902,289 A | 2/1990 | Yannas | |
| 4,906,423 A | 3/1990 | Frisch | |
| 4,931,287 A | 6/1990 | Bae et al. | |
| 4,932,353 A | 6/1990 | Kawata et al. | |
| 4,941,870 A | 7/1990 | Okada et al. | |
| 4,943,346 A | 7/1990 | Mattelin | |
| 4,950,227 A | 8/1990 | Savin et al. | |
| 4,955,899 A | 9/1990 | Della Corna et al. | |
| 4,967,606 A | 11/1990 | Wells et al. | |
| 4,977,901 A | 12/1990 | Ofstead | |
| 4,988,356 A | 1/1991 | Crittenden et al. | |
| 4,994,033 A | 2/1991 | Shockey et al. | |
| 4,994,298 A | 2/1991 | Yasuda | |
| 4,994,560 A | 2/1991 | Kruper, Jr. et al. | |
| 5,015,505 A | 5/1991 | Cetnar | |
| 5,019,090 A | 5/1991 | Pinchuk | |
| 5,019,096 A | 5/1991 | Fox, Jr. et al. | |
| 5,028,597 A | 7/1991 | Kodama et al. | |
| 5,037,392 A | 8/1991 | Hillstead | |
| 5,037,427 A | 8/1991 | Harada et al. | |
| 5,040,548 A | 8/1991 | Yock | |
| 5,047,050 A | 9/1991 | Arpesani | |
| 5,049,132 A | 9/1991 | Shaffer et al. | |
| 5,053,048 A | 10/1991 | Pinchuk | |
| 5,059,166 A | 10/1991 | Fischell | |
| 5,059,169 A | 10/1991 | Zilber | |
| 5,059,211 A | 10/1991 | Stack et al. | |
| 5,062,829 A | 11/1991 | Pryor et al. | |
| 5,064,435 A | 11/1991 | Porter | |
| 5,078,720 A | 1/1992 | Burton et al. | |
| 5,081,394 A | 1/1992 | Morishita et al. | |
| 5,084,065 A | 1/1992 | Weldon et al. | |
| 5,085,629 A | 2/1992 | Goldberg et al. | |
| 5,087,244 A | 2/1992 | Wolinsky et al. | |
| 5,087,394 A | 2/1992 | Keith | |
| 5,100,429 A | 3/1992 | Sinofsky et al. | |
| 5,100,992 A | 3/1992 | Cohn et al. | |
| 5,102,402 A | 4/1992 | Dror et al. | |
| 5,104,410 A | 4/1992 | Chowdhary | |
| 5,108,416 A | 4/1992 | Ryan et al. | |
| 5,108,417 A | 4/1992 | Sawyer | |
| 5,108,755 A | 4/1992 | Daniels et al. | |
| 5,112,457 A | 5/1992 | Marchant | |
| 5,116,318 A | 5/1992 | Hillstead | |
| 5,116,365 A | 5/1992 | Hillstead | |
| 5,123,917 A | 6/1992 | Lee | |
| 5,127,362 A | 7/1992 | Iwatsu et al. | |
| 5,133,742 A | 7/1992 | Pinchuk | |
| 5,134,192 A | 7/1992 | Feijen et al. | |
| 5,147,370 A | 9/1992 | McNamara et al. | |
| 5,156,623 A | 10/1992 | Hakamatsuka et al. | |
| 5,156,911 A | 10/1992 | Stewart | |
| 5,158,548 A | 10/1992 | Lau et al. | |
| 5,163,951 A | 11/1992 | Pinchuk et al. | |
| 5,163,952 A | 11/1992 | Froix | |
| 5,163,958 A | 11/1992 | Pinchuk | |
| 5,165,919 A | 11/1992 | Sasaki et al. | |
| 5,167,614 A | 12/1992 | Tessmann et al. | |
| 5,171,445 A | 12/1992 | Zepf | |
| 5,176,638 A | 1/1993 | Don Michael | |
| 5,188,734 A | 2/1993 | Zepf | |
| 5,192,311 A | 3/1993 | King et al. | |
| 5,197,977 A | 3/1993 | Hoffman, Jr. et al. | |
| 5,205,822 A | 4/1993 | Johnson et al. | |
| 5,213,561 A | 5/1993 | Weinstein et al. | |
| 5,213,576 A | 5/1993 | Abiuso et al. | |
| 5,219,980 A | 6/1993 | Swidler | |
| 5,222,971 A | 6/1993 | Willard et al. | |
| 5,225,750 A | 7/1993 | Higuchi et al. | |
| 5,226,889 A | 7/1993 | Sheiban | |
| 5,226,913 A | 7/1993 | Pinchuk | |
| 5,229,045 A | 7/1993 | Soldani | |
| 5,229,172 A | 7/1993 | Cahalan et al. | |
| 5,232,444 A | 8/1993 | Just et al. | |
| 5,234,456 A | 8/1993 | Silvestrini | |
| 5,234,457 A | 8/1993 | Andersen | |
| 5,236,447 A | 8/1993 | Kubo et al. | |
| 5,242,399 A | 9/1993 | Lau et al. | |
| 5,254,089 A | 10/1993 | Wang | |
| 5,254,091 A | 10/1993 | Aliahmad et al. | |
| 5,258,020 A | 11/1993 | Froix | |
| 5,258,419 A | 11/1993 | Rolando et al. | |
| 5,264,221 A * | 11/1993 | Tagawa et al. | 424/450 |
| 5,269,802 A | 12/1993 | Garber | |
| 5,272,012 A | 12/1993 | Opolski | |
| 5,278,200 A | 1/1994 | Coury et al. | |
| 5,279,594 A | 1/1994 | Jackson | |
| 5,282,823 A | 2/1994 | Schwartz et al. | |
| 5,282,860 A | 2/1994 | Matsuno et al. | |
| 5,286,254 A | 2/1994 | Shapland et al. | |
| 5,289,831 A | 3/1994 | Bosley | |
| 5,290,271 A | 3/1994 | Jernberg | |
| 5,292,516 A | 3/1994 | Viegas et al. | |
| 5,298,260 A | 3/1994 | Viegas et al. | |
| 5,300,295 A | 4/1994 | Viegas et al. | |
| 5,304,200 A | 4/1994 | Spaulding | |
| 5,306,250 A | 4/1994 | March et al. | |
| 5,306,286 A | 4/1994 | Stack et al. | |
| 5,306,294 A | 4/1994 | Winston et al. | |
| 5,306,501 A | 4/1994 | Viegas et al. | |
| 5,306,786 A | 4/1994 | Moens et al. | |
| 5,308,641 A | 5/1994 | Cahalan et al. | |
| 5,314,472 A | 5/1994 | Fontaine | |
| 5,318,531 A | 6/1994 | Leone | |
| 5,328,471 A | 7/1994 | Slepian | |
| 5,330,500 A | 7/1994 | Song | |
| 5,330,768 A | 7/1994 | Park et al. | |
| 5,336,518 A | 8/1994 | Narayanan et al. | |
| 5,342,283 A | 8/1994 | Good | |
| 5,342,348 A | 8/1994 | Kaplan | |
| 5,342,395 A | 8/1994 | Jarrett et al. | |
| 5,342,621 A | 8/1994 | Eury | |
| 5,344,426 A | 9/1994 | Lau et al. | |
| 5,344,455 A | 9/1994 | Keogh et al. | |
| 5,350,800 A | 9/1994 | Verhoeven et al. | |
| 5,356,433 A | 10/1994 | Rowland et al. | |
| 5,360,401 A | 11/1994 | Turnland et al. | |
| 5,360,443 A | 11/1994 | Barone et al. | |
| 5,364,354 A | 11/1994 | Walker et al. | |
| 5,366,504 A | 11/1994 | Andersen et al. | |
| 5,368,560 A | 11/1994 | Rambo et al. | |
| 5,370,684 A | 12/1994 | Vallana et al. | |
| 5,380,299 A | 1/1995 | Fearnot et al. | |
| 5,383,925 A | 1/1995 | Schmitt | |
| 5,383,927 A | 1/1995 | DeGoicoechea et al. | |
| 5,385,580 A | 1/1995 | Schmitt | |
| 5,387,450 A | 2/1995 | Stewart | |
| 5,389,106 A | 2/1995 | Tower | |
| 5,399,666 A | 3/1995 | Ford | |
| 5,405,472 A | 4/1995 | Leone | |
| 5,409,495 A | 4/1995 | Osborn | |
| 5,411,466 A | 5/1995 | Hess | |
| 5,411,477 A | 5/1995 | Saab | |
| 5,411,730 A * | 5/1995 | Kirpotin et al. | 424/9.322 |
| 5,412,035 A | 5/1995 | Schmitt et al. | |
| 5,415,938 A | 5/1995 | Cahalan et al. | |
| 5,417,981 A | 5/1995 | Endo et al. | |
| 5,423,849 A | 6/1995 | Engelson et al. | |
| 5,423,885 A | 6/1995 | Williams | |
| 5,429,618 A | 7/1995 | Keogh | |
| 5,441,515 A | 8/1995 | Khosravi et al. | |
| 5,441,746 A * | 8/1995 | Chagnon | 424/450 |
| 5,443,458 A | 8/1995 | Eury et al. | |
| 5,443,496 A | 8/1995 | Schwartz et al. | |
| 5,443,500 A | 8/1995 | Sigwart | |
| 5,445,646 A | 8/1995 | Euteneuer et al. | |
| 5,447,724 A | 9/1995 | Helmus et al. | |
| 5,451,233 A | 9/1995 | Yock | |
| 5,455,040 A | 10/1995 | Marchant | |
| 5,456,661 A | 10/1995 | Narciso, Jr. | |
| 5,456,713 A | 10/1995 | Chuter | |
| 5,458,615 A | 10/1995 | Klemm et al. | |
| 5,460,610 A | 10/1995 | Michael | |
| 5,462,990 A | 10/1995 | Hubbell et al. | |
| 5,464,450 A | 11/1995 | Buscemi et al. | |

| Patent | Date | Inventor |
|---|---|---|
| 5,464,650 A | 11/1995 | Berg et al. |
| 5,470,313 A | 11/1995 | Crocker et al. |
| 5,470,603 A | 11/1995 | Staniforth et al. |
| 5,476,476 A | 12/1995 | Hillstead |
| 5,476,509 A | 12/1995 | Keogh et al. |
| 5,485,496 A | 1/1996 | Lee et al. |
| 5,496,346 A | 3/1996 | Horzewski et al. |
| 5,500,013 A | 3/1996 | Buscemi et al. |
| 5,501,227 A | 3/1996 | Yock |
| 5,502,158 A | 3/1996 | Sinclair et al. |
| 5,507,768 A | 4/1996 | Lau et al. |
| 5,511,726 A | 4/1996 | Greenspan et al. |
| 5,514,154 A | 5/1996 | Lau et al. |
| 5,514,379 A | 5/1996 | Weissleder et al. |
| 5,516,560 A | 5/1996 | Harayama et al. |
| 5,516,881 A | 5/1996 | Lee et al. |
| 5,527,337 A | 6/1996 | Stack et al. |
| 5,537,729 A | 7/1996 | Kolobow |
| 5,538,493 A | 7/1996 | Gerken et al. |
| 5,545,209 A | 8/1996 | Roberts et al. |
| 5,545,408 A | 8/1996 | Trigg et al. |
| 5,551,954 A | 9/1996 | Buscemi et al. |
| 5,554,120 A | 9/1996 | Chen et al. |
| 5,554,182 A | 9/1996 | Dinh et al. |
| 5,556,413 A | 9/1996 | Lam |
| 5,558,642 A | 9/1996 | Schweich, Jr. et al. |
| 5,562,728 A | 10/1996 | Lazarus et al. |
| 5,569,463 A | 10/1996 | Helmus et al. |
| 5,571,135 A | 11/1996 | Fraser et al. |
| 5,571,166 A | 11/1996 | Dinh et al. |
| 5,571,567 A | 11/1996 | Shah |
| 5,578,046 A | 11/1996 | Liu et al. |
| 5,578,073 A | 11/1996 | Haimovich et al. |
| 5,584,877 A | 12/1996 | Miyake et al. |
| 5,588,962 A | 12/1996 | Nicholas et al. |
| 5,591,199 A | 1/1997 | Porter et al. |
| 5,591,224 A | 1/1997 | Schwartz et al. |
| 5,591,227 A | 1/1997 | Dinh et al. |
| 5,591,607 A | 1/1997 | Gryaznov et al. |
| 5,593,403 A | 1/1997 | Buscemi |
| 5,593,434 A | 1/1997 | Williams |
| 5,595,722 A | 1/1997 | Grainger et al. |
| 5,599,301 A | 2/1997 | Jacobs et al. |
| 5,599,307 A | 2/1997 | Bacher et al. |
| 5,599,352 A | 2/1997 | Dinh et al. |
| 5,599,922 A | 2/1997 | Gryaznov et al. |
| 5,605,696 A | 2/1997 | Eury et al. |
| 5,607,442 A | 3/1997 | Fischell et al. |
| 5,607,467 A | 3/1997 | Froix |
| 5,609,629 A | 3/1997 | Fearnot et al. |
| 5,610,241 A | 3/1997 | Lee et al. |
| 5,611,775 A | 3/1997 | Machold et al. |
| 5,616,338 A | 4/1997 | Fox, Jr. et al. |
| 5,618,298 A | 4/1997 | Simon |
| 5,618,299 A | 4/1997 | Khosravi et al. |
| 5,620,420 A | 4/1997 | Kriesel |
| 5,624,411 A | 4/1997 | Tuch |
| 5,628,730 A | 5/1997 | Shapland et al. |
| 5,628,755 A | 5/1997 | Heller et al. |
| 5,628,781 A | 5/1997 | Williams et al. |
| 5,628,785 A | 5/1997 | Schwartz et al. |
| 5,628,786 A | 5/1997 | Banas et al. |
| 5,629,077 A | 5/1997 | Turnlund et al. |
| 5,631,135 A | 5/1997 | Gryaznov et al. |
| 5,632,771 A | 5/1997 | Boatman et al. |
| 5,632,840 A | 5/1997 | Campbell |
| 5,637,113 A | 6/1997 | Tartaglia et al. |
| 5,644,020 A | 7/1997 | Timmermann et al. |
| 5,645,559 A | 7/1997 | Hachtman et al. |
| 5,649,951 A | 7/1997 | Davidson |
| 5,649,977 A | 7/1997 | Campbell |
| 5,653,691 A | 8/1997 | Rupp et al. |
| 5,656,080 A | 8/1997 | Staniforth et al. |
| 5,656,082 A | 8/1997 | Takatsuki et al. |
| 5,658,995 A | 8/1997 | Kohn et al. |
| 5,667,523 A | 9/1997 | Bynon et al. |
| 5,667,767 A | 9/1997 | Greff et al. |
| 5,667,796 A | 9/1997 | Otten |
| 5,670,558 A | 9/1997 | Onishi et al. |
| 5,674,242 A | 10/1997 | Phan et al. |
| 5,679,400 A | 10/1997 | Tuch |
| 5,693,085 A | 12/1997 | Buirge et al. |
| 5,693,376 A | 12/1997 | Fetherston et al. |
| 5,695,498 A | 12/1997 | Tower |
| 5,695,810 A | 12/1997 | Dubin et al. |
| 5,697,967 A | 12/1997 | Dinh et al. |
| 5,700,286 A | 12/1997 | Tartaglia et al. |
| 5,702,754 A | 12/1997 | Zhong |
| 5,702,818 A | 12/1997 | Cahalan et al. |
| 5,707,385 A | 1/1998 | Williams |
| 5,711,763 A | 1/1998 | Nonami et al. |
| 5,711,812 A | 1/1998 | Chapek et al. |
| 5,711,958 A | 1/1998 | Cohn et al. |
| 5,713,949 A | 2/1998 | Jayaraman |
| 5,716,981 A | 2/1998 | Hunter et al. |
| 5,718,726 A | 2/1998 | Amon et al. |
| 5,720,726 A | 2/1998 | Marcadis et al. |
| 5,721,131 A | 2/1998 | Rudolph et al. |
| 5,722,984 A | 3/1998 | Fischell et al. |
| 5,723,219 A | 3/1998 | Kolluri et al. |
| 5,725,549 A | 3/1998 | Lam |
| 5,726,297 A | 3/1998 | Gryaznov et al. |
| 5,728,068 A | 3/1998 | Leone et al. |
| 5,728,751 A | 3/1998 | Patnaik |
| 5,730,698 A | 3/1998 | Fischell et al. |
| 5,733,326 A | 3/1998 | Tomonto et al. |
| 5,733,327 A | 3/1998 | Igaki et al. |
| 5,733,330 A | 3/1998 | Cox |
| 5,733,564 A | 3/1998 | Lehtinen |
| 5,733,925 A | 3/1998 | Kunz et al. |
| 5,735,897 A | 4/1998 | Buirge |
| 5,741,554 A | 4/1998 | Tisone |
| 5,741,881 A | 4/1998 | Patnaik |
| 5,746,745 A | 5/1998 | Abele et al. |
| 5,746,998 A | 5/1998 | Torchilin et al. |
| 5,756,457 A | 5/1998 | Wang et al. |
| 5,756,476 A | 5/1998 | Epstein et al. |
| 5,759,205 A | 6/1998 | Valentini |
| 5,759,474 A | 6/1998 | Rupp et al. |
| 5,765,682 A | 6/1998 | Bley et al. |
| 5,766,204 A | 6/1998 | Porter et al. |
| 5,766,239 A | 6/1998 | Cox |
| 5,766,710 A | 6/1998 | Turnlund et al. |
| 5,769,883 A | 6/1998 | Buscemi et al. |
| 5,769,884 A | 6/1998 | Solovay |
| 5,770,609 A | 6/1998 | Grainger et al. |
| 5,772,864 A | 6/1998 | Møller et al. |
| 5,776,184 A | 7/1998 | Tuch |
| 5,780,807 A | 7/1998 | Saunders |
| 5,782,742 A | 7/1998 | Crocker et al. |
| 5,783,657 A | 7/1998 | Pavlin et al. |
| 5,788,626 A | 8/1998 | Thompson |
| 5,788,979 A | 8/1998 | Alt et al. |
| 5,800,392 A | 9/1998 | Racchini |
| 5,800,516 A | 9/1998 | Fine et al. |
| 5,804,318 A | 9/1998 | Pinchuk et al. |
| 5,807,244 A | 9/1998 | Barot |
| 5,810,871 A | 9/1998 | Tuckey et al. |
| 5,810,873 A | 9/1998 | Morales |
| 5,811,151 A | 9/1998 | Hendriks et al. |
| 5,811,447 A | 9/1998 | Kunz et al. |
| 5,820,917 A | 10/1998 | Tuch |
| 5,823,996 A | 10/1998 | Sparks |
| 5,824,048 A | 10/1998 | Tuch |
| 5,824,049 A | 10/1998 | Ragheb et al. |
| 5,824,056 A | 10/1998 | Rosenberg |
| 5,826,586 A | 10/1998 | Mishra et al. |
| 5,830,178 A | 11/1998 | Jones et al. |
| 5,830,179 A | 11/1998 | Mikus et al. |
| 5,830,217 A | 11/1998 | Ryan |
| 5,830,461 A | 11/1998 | Billiar |
| 5,830,879 A | 11/1998 | Isner |
| 5,833,644 A | 11/1998 | Zadno-Azizi et al. |
| 5,833,651 A | 11/1998 | Donovan et al. |
| 5,833,659 A | 11/1998 | Kranys |
| 5,834,582 A | 11/1998 | Sinclair et al. |
| 5,836,962 A | 11/1998 | Gianotti |
| 5,836,965 A | 11/1998 | Jendersee et al. |

| | | | | | | |
|---|---|---|---|---|---|---|
| 5,837,008 A | 11/1998 | Berg et al. | | 5,969,422 A | 10/1999 | Ting et al. |
| 5,837,313 A | 11/1998 | Ding et al. | | 5,971,954 A | 10/1999 | Conway et al. |
| 5,837,835 A | 11/1998 | Gryaznov et al. | | 5,972,027 A | 10/1999 | Johnson |
| 5,840,009 A | 11/1998 | Fischell et al. | | 5,972,029 A | 10/1999 | Fuisz |
| 5,840,083 A | 11/1998 | Braach-Maksvytis | | 5,972,505 A | 10/1999 | Phillips et al. |
| 5,843,033 A | 12/1998 | Ropiak | | 5,976,155 A | 11/1999 | Foreman et al. |
| 5,843,119 A | 12/1998 | Schulewitz | | 5,976,182 A | 11/1999 | Cox |
| 5,843,172 A | 12/1998 | Yan | | 5,980,564 A | 11/1999 | Stinson |
| 5,846,247 A | 12/1998 | Unsworth et al. | | 5,980,928 A | 11/1999 | Terry |
| 5,849,859 A | 12/1998 | Acemoglu | | 5,980,972 A | 11/1999 | Ding |
| 5,851,508 A | 12/1998 | Greff et al. | | 5,981,568 A | 11/1999 | Kunz et al. |
| 5,853,408 A | 12/1998 | Muni | | 5,984,449 A | 11/1999 | Tajika et al. |
| 5,854,207 A | 12/1998 | Lee et al. | | 5,986,043 A | 11/1999 | Hubbell et al. |
| 5,854,376 A | 12/1998 | Higashi | | 5,986,169 A | 11/1999 | Gjunter |
| 5,855,598 A | 1/1999 | Pinchuk | | 5,997,468 A | 12/1999 | Wolff et al. |
| 5,855,612 A | 1/1999 | Ohthuki et al. | | 5,997,517 A | 12/1999 | Whitbourne |
| 5,855,618 A | 1/1999 | Patnaik et al. | | 6,010,445 A | 1/2000 | Armini et al. |
| 5,857,998 A | 1/1999 | Barry | | 6,010,530 A | 1/2000 | Goicoechea |
| 5,858,556 A | 1/1999 | Eckhart et al. | | 6,010,573 A | 1/2000 | Bowlin |
| 5,858,746 A | 1/1999 | Hubbell et al. | | 6,011,125 A | 1/2000 | Lohmeijer et al. |
| 5,858,990 A | 1/1999 | Walsh | | 6,013,099 A | 1/2000 | Dinh et al. |
| 5,860,954 A | 1/1999 | Ropiak | | 6,015,541 A | 1/2000 | Greff et al. |
| 5,865,814 A | 2/1999 | Tuch | | 6,019,789 A | 2/2000 | Dinh et al. |
| 5,866,113 A | 2/1999 | Hendriks et al. | | 6,024,918 A | 2/2000 | Hendriks et al. |
| 5,868,781 A | 2/1999 | Killion | | 6,027,510 A | 2/2000 | Alt |
| 5,869,127 A | 2/1999 | Zhong | | 6,027,526 A | 2/2000 | Limon et al. |
| 5,871,436 A | 2/1999 | Eury | | 6,030,371 A | 2/2000 | Pursley |
| 5,871,437 A | 2/1999 | Alt | | 6,033,582 A | 3/2000 | Lee et al. |
| 5,873,904 A | 2/1999 | Ragheb et al. | | 6,033,719 A | 3/2000 | Keogh |
| 5,874,101 A | 2/1999 | Zhong et al. | | 6,034,204 A | 3/2000 | Mohr et al. |
| 5,874,109 A | 2/1999 | Ducheyne et al. | | 6,042,606 A | 3/2000 | Frantzen |
| 5,874,165 A | 2/1999 | Drumheller | | 6,042,875 A | 3/2000 | Ding et al. |
| 5,874,355 A | 2/1999 | Huang et al. | | 6,045,899 A | 4/2000 | Wang et al. |
| 5,876,426 A | 3/1999 | Kume et al. | | 6,048,964 A | 4/2000 | Lee et al. |
| 5,876,433 A | 3/1999 | Lunn | | 6,051,021 A | 4/2000 | Frid |
| 5,876,743 A | 3/1999 | Ibsen et al. | | 6,051,576 A | 4/2000 | Ashton et al. |
| 5,877,224 A | 3/1999 | Brocchini et al. | | 6,051,648 A | 4/2000 | Rhee et al. |
| 5,877,263 A | 3/1999 | Patnaik et al. | | 6,054,553 A | 4/2000 | Groth et al. |
| 5,879,713 A | 3/1999 | Roth et al. | | 6,056,906 A | 5/2000 | Werneth et al. |
| 5,883,011 A | 3/1999 | Lin et al. | | 6,056,993 A | 5/2000 | Leidner et al. |
| 5,888,533 A | 3/1999 | Dunn | | 6,059,752 A | 5/2000 | Segal |
| 5,891,192 A | 4/1999 | Murayama et al. | | 6,059,810 A | 5/2000 | Brown et al. |
| 5,893,840 A | 4/1999 | Hull et al. | | 6,060,451 A | 5/2000 | DiMaio et al. |
| 5,893,852 A | 4/1999 | Morales | | 6,060,518 A | 5/2000 | Kabanov et al. |
| 5,895,407 A | 4/1999 | Jayaraman | | 6,063,092 A | 5/2000 | Shin |
| 5,897,911 A | 4/1999 | Loeffler | | 6,066,156 A | 5/2000 | Yan |
| 5,897,955 A | 4/1999 | Drumheller | | 6,071,266 A | 6/2000 | Kelley |
| 5,898,178 A | 4/1999 | Bunker | | 6,071,305 A | 6/2000 | Brown et al. |
| 5,902,631 A | 5/1999 | Wang et al. | | 6,074,659 A | 6/2000 | Kunz et al. |
| 5,902,875 A | 5/1999 | Roby et al. | | 6,080,099 A | 6/2000 | Slater et al. |
| 5,905,168 A | 5/1999 | Dos Santos et al. | | 6,080,177 A | 6/2000 | Igaki et al. |
| 5,906,759 A | 5/1999 | Richter | | 6,080,190 A | 6/2000 | Schwartz |
| 5,910,564 A | 6/1999 | Gruning et al. | | 6,080,488 A | 6/2000 | Hostettler et al. |
| 5,914,182 A | 6/1999 | Drumheller | | 6,083,258 A | 7/2000 | Yadav |
| 5,914,387 A | 6/1999 | Roby et al. | | 6,086,610 A | 7/2000 | Duerig et al. |
| 5,916,234 A | 6/1999 | Lam | | 6,090,330 A | 7/2000 | Gawa et al. |
| 5,916,870 A | 6/1999 | Lee et al. | | 6,093,199 A | 7/2000 | Brown et al. |
| 5,919,893 A | 7/1999 | Roby et al. | | 6,093,463 A | 7/2000 | Thakrar |
| 5,921,416 A | 7/1999 | Uchara | | 6,096,070 A | 8/2000 | Ragheb et al. |
| 5,922,005 A | 7/1999 | Richter et al. | | 6,096,525 A | 8/2000 | Patnaik |
| 5,922,393 A | 7/1999 | Jayaraman | | 6,099,455 A | 8/2000 | Columbo et al. |
| 5,925,552 A | 7/1999 | Keogh et al. | | 6,099,559 A | 8/2000 | Nolting |
| 5,925,720 A | 7/1999 | Kataoka et al. | | 6,099,561 A | 8/2000 | Alt |
| 5,928,916 A | 7/1999 | Keogh | | 6,099,562 A | 8/2000 | Ding et al. |
| 5,932,299 A | 8/1999 | Katoot | | 6,103,230 A | 8/2000 | Billiar et al. |
| 5,935,135 A | 8/1999 | Bramfitt et al. | | 6,106,454 A | 8/2000 | Berg et al. |
| 5,942,209 A | 8/1999 | Leavitt et al. | | 6,106,530 A | 8/2000 | Harada |
| 5,947,993 A | 9/1999 | Morales | | 6,106,889 A | 8/2000 | Beavers et al. |
| 5,948,018 A | 9/1999 | Dereume et al. | | 6,107,416 A | 8/2000 | Patnaik et al. |
| 5,948,428 A | 9/1999 | Lee et al. | | 6,110,180 A | 8/2000 | Foreman et al. |
| 5,951,881 A | 9/1999 | Rogers et al. | | 6,110,188 A | 8/2000 | Narciso, Jr. |
| 5,954,744 A | 9/1999 | Phan et al. | | 6,110,483 A | 8/2000 | Whitbourne et al. |
| 5,955,509 A | 9/1999 | Webber et al. | | 6,113,629 A | 9/2000 | Ken |
| 5,957,975 A | 9/1999 | Lafont et al. | | 6,117,479 A | 9/2000 | Hogan et al. |
| 5,958,385 A | 9/1999 | Tondeur et al. | | 6,117,979 A | 9/2000 | Hendriks et al. |
| 5,962,138 A | 10/1999 | Kolluri et al. | | 6,120,477 A | 9/2000 | Campbell et al. |
| 5,965,720 A | 10/1999 | Gryaznov et al. | | 6,120,491 A | 9/2000 | Kohn et al. |
| 5,968,091 A | 10/1999 | Pinchuk et al. | | 6,120,535 A | 9/2000 | McDonald et al. |
| 5,968,092 A | 10/1999 | Buscemi et al. | | 6,120,536 A | 9/2000 | Ding et al. |

| | | |
|---|---|---|
| 6,120,788 A | 9/2000 | Barrows |
| 6,120,847 A | 9/2000 | Yang et al. |
| 6,120,904 A | 9/2000 | Hostettler et al. |
| 6,121,027 A | 9/2000 | Clapper et al. |
| 6,121,425 A * | 9/2000 | Hainfeld et al. ........... 530/391.5 |
| 6,123,712 A | 9/2000 | Di Caprio et al. |
| 6,125,523 A | 10/2000 | Brown et al. |
| 6,126,686 A | 10/2000 | Badylak et al. |
| 6,127,173 A | 10/2000 | Eckstein et al. |
| 6,129,761 A | 10/2000 | Hubbell |
| 6,129,928 A | 10/2000 | Sarangapani et al. |
| 6,132,809 A | 10/2000 | Hynes et al. |
| 6,136,333 A | 10/2000 | Cohn et al. |
| 6,140,127 A | 10/2000 | Sprague |
| 6,140,431 A | 10/2000 | Kinker et al. |
| 6,143,354 A | 11/2000 | Koulik et al. |
| 6,143,370 A | 11/2000 | Panagiotou et al. |
| 6,149,574 A | 11/2000 | Trauthen et al. |
| 6,150,630 A | 11/2000 | Perry et al. |
| 6,153,252 A | 11/2000 | Hossainy et al. |
| 6,156,373 A | 12/2000 | Zhong et al. |
| 6,159,227 A | 12/2000 | Di Caprio et al. |
| 6,159,229 A | 12/2000 | Jendersee et al. |
| 6,159,951 A | 12/2000 | Karpeisky et al. |
| 6,159,978 A | 12/2000 | Myers et al. |
| 6,160,084 A | 12/2000 | Langer et al. |
| 6,165,212 A | 12/2000 | Dereume et al. |
| 6,166,130 A | 12/2000 | Rhee et al. |
| 6,168,617 B1 | 1/2001 | Blaeser et al. |
| 6,168,619 B1 | 1/2001 | Dinh et al. |
| 6,169,170 B1 | 1/2001 | Gryaznov et al. |
| 6,171,609 B1 | 1/2001 | Kunz |
| 6,172,167 B1 | 1/2001 | Stapert et al. |
| 6,174,316 B1 | 1/2001 | Tuckey et al. |
| 6,174,330 B1 | 1/2001 | Stinson |
| 6,177,523 B1 | 1/2001 | Reich et al. |
| 6,180,632 B1 | 1/2001 | Myers et al. |
| 6,183,505 B1 | 2/2001 | Mohn, Jr. et al. |
| 6,187,045 B1 | 2/2001 | Fehring et al. |
| 6,193,727 B1 | 2/2001 | Foreman et al. |
| 6,203,551 B1 | 3/2001 | Wu |
| 6,209,621 B1 | 4/2001 | Treacy |
| 6,210,715 B1 | 4/2001 | Starling et al. |
| 6,211,249 B1 | 4/2001 | Cohn et al. |
| 6,214,115 B1 | 4/2001 | Taylor et al. |
| 6,214,407 B1 | 4/2001 | Laube et al. |
| 6,214,901 B1 | 4/2001 | Chudzik et al. |
| 6,217,586 B1 | 4/2001 | Mackenzie |
| 6,217,721 B1 | 4/2001 | Xu et al. |
| 6,224,626 B1 | 5/2001 | Steinke |
| 6,224,675 B1 | 5/2001 | Prentice et al. |
| 6,224,894 B1 | 5/2001 | Jamiolkowski et al. |
| 6,228,845 B1 | 5/2001 | Donovan et al. |
| 6,231,590 B1 | 5/2001 | Slaikeu et al. |
| 6,231,600 B1 | 5/2001 | Zhong |
| 6,240,616 B1 | 6/2001 | Yan |
| 6,242,041 B1 | 6/2001 | Katoot et al. |
| 6,245,076 B1 | 6/2001 | Yan |
| 6,245,099 B1 | 6/2001 | Edwin et al. |
| 6,245,103 B1 | 6/2001 | Stinson |
| 6,245,753 B1 | 6/2001 | Byun et al. |
| 6,245,760 B1 | 6/2001 | He et al. |
| 6,248,129 B1 | 6/2001 | Froix |
| 6,248,344 B1 | 6/2001 | Ylanen et al. |
| 6,251,135 B1 | 6/2001 | Stinson et al. |
| 6,251,136 B1 | 6/2001 | Guruwaiya et al. |
| 6,251,142 B1 | 6/2001 | Bernacca et al. |
| 6,253,443 B1 | 7/2001 | Johnson |
| 6,254,632 B1 | 7/2001 | Wu et al. |
| 6,258,099 B1 | 7/2001 | Mareiro et al. |
| 6,258,121 B1 | 7/2001 | Yang et al. |
| 6,258,371 B1 | 7/2001 | Koulik et al. |
| 6,262,034 B1 | 7/2001 | Mathiowitz et al. |
| 6,270,788 B1 | 8/2001 | Koulik et al. |
| 6,273,850 B1 | 8/2001 | Gambale |
| 6,273,913 B1 | 8/2001 | Wright et al. |
| 6,277,110 B1 | 8/2001 | Morales |
| 6,277,449 B1 | 8/2001 | Kolluri et al. |
| 6,279,368 B1 | 8/2001 | Escano et al. |
| 6,281,262 B1 | 8/2001 | Shikinami |
| 6,283,947 B1 | 9/2001 | Mirzaee |
| 6,283,949 B1 | 9/2001 | Roorda |
| 6,284,305 B1 | 9/2001 | Ding et al. |
| 6,284,333 B1 | 9/2001 | Wang et al. |
| 6,287,332 B1 | 9/2001 | Bolz et al. |
| 6,287,628 B1 | 9/2001 | Hossainy et al. |
| 6,290,721 B1 | 9/2001 | Heath |
| 6,293,966 B1 | 9/2001 | Frantzen |
| 6,294,836 B1 | 9/2001 | Paranjpe et al. |
| 6,296,603 B1 | 10/2001 | Turnlund et al. |
| 6,299,604 B1 | 10/2001 | Ragheb et al. |
| 6,303,901 B1 | 10/2001 | Perry et al. |
| 6,306,176 B1 | 10/2001 | Whitbourne |
| 6,312,459 B1 | 11/2001 | Huang et al. |
| 6,319,520 B1 | 11/2001 | Wuthrich et al. |
| 6,322,588 B1 | 11/2001 | Ogle et al. |
| 6,322,847 B1 | 11/2001 | Zhong et al. |
| 6,327,772 B1 | 12/2001 | Zadno-Azizi et al. |
| 6,331,313 B1 | 12/2001 | Wong et al. |
| 6,335,029 B1 | 1/2002 | Kamath et al. |
| 6,344,035 B1 | 2/2002 | Chudzik et al. |
| 6,346,110 B2 | 2/2002 | Wu |
| 6,358,556 B1 | 3/2002 | Ding et al. |
| 6,362,099 B1 | 3/2002 | Gandikota et al. |
| 6,364,903 B2 | 4/2002 | Tseng et al. |
| 6,375,458 B1 | 4/2002 | Moorleghem et al. |
| 6,375,826 B1 | 4/2002 | Wang et al. |
| 6,379,379 B1 | 4/2002 | Wang |
| 6,379,381 B1 | 4/2002 | Hossainy et al. |
| 6,387,118 B1 | 5/2002 | Hanson |
| 6,387,121 B1 | 5/2002 | Alt |
| 6,387,379 B1 | 5/2002 | Goldberg et al. |
| 6,388,043 B1 | 5/2002 | Langer et al. |
| 6,395,325 B1 | 5/2002 | Hedge et al. |
| 6,395,326 B1 | 5/2002 | Castro et al. |
| 6,406,738 B1 | 6/2002 | Hogan et al. |
| 6,409,761 B1 | 6/2002 | Jang |
| 6,413,272 B1 | 7/2002 | Igaki |
| 6,419,692 B1 | 7/2002 | Yang et al. |
| 6,420,189 B1 | 7/2002 | Lopatin |
| 6,423,092 B2 | 7/2002 | Datta et al. |
| 6,436,816 B1 | 8/2002 | Lee et al. |
| 6,444,567 B1 | 9/2002 | Besser et al. |
| 6,447,835 B1 | 9/2002 | Wang et al. |
| 6,451,373 B1 | 9/2002 | Hossainy et al. |
| 6,454,738 B1 | 9/2002 | Tran et al. |
| 6,455,424 B1 | 9/2002 | McTeer et al. |
| 6,461,632 B1 | 10/2002 | Gogolewski |
| 6,462,284 B1 | 10/2002 | Hashimoto |
| 6,464,720 B2 | 10/2002 | Boatman et al. |
| 6,468,906 B1 | 10/2002 | Chan et al. |
| 6,475,779 B2 | 11/2002 | Mathiowitz et al. |
| 6,479,565 B1 | 11/2002 | Stanley |
| 6,481,262 B2 | 11/2002 | Ching et al. |
| 6,482,834 B2 | 11/2002 | Spada et al. |
| 6,485,512 B1 | 11/2002 | Cheng |
| 6,488,701 B1 | 12/2002 | Nolting et al. |
| 6,488,773 B1 | 12/2002 | Ehrhardt et al. |
| 6,491,666 B1 | 12/2002 | Santini, Jr. et al. |
| 6,492,615 B1 | 12/2002 | Flanagan |
| 6,494,862 B1 | 12/2002 | Ray et al. |
| 6,494,908 B1 | 12/2002 | Huxel et al. |
| 6,495,156 B2 | 12/2002 | Wenz et al. |
| 6,495,200 B1 | 12/2002 | Chan et al. |
| 6,503,538 B1 | 1/2003 | Chu et al. |
| 6,503,556 B1 | 1/2003 | Harish et al. |
| 6,503,954 B1 | 1/2003 | Bhat et al. |
| 6,504,307 B1 | 1/2003 | Malik et al. |
| 6,506,437 B1 | 1/2003 | Harish et al. |
| 6,510,722 B1 | 1/2003 | Ching et al. |
| 6,511,748 B1 | 1/2003 | Barrows |
| 6,517,888 B1 | 2/2003 | Weber |
| 6,517,889 B1 | 2/2003 | Jayaraman |
| 6,521,284 B1 | 2/2003 | Parsons et al. |
| 6,524,232 B1 | 2/2003 | Tang et al. |
| 6,524,347 B1 | 2/2003 | Myers et al. |
| 6,527,801 B1 | 3/2003 | Dutta |
| 6,527,863 B1 | 3/2003 | Pacetti et al. |

| Patent | Kind | Date | Inventor |
|---|---|---|---|
| 6,528,526 | B1 | 3/2003 | Myers et al. |
| 6,530,944 | B2 | 3/2003 | West et al. |
| 6,530,950 | B1 | 3/2003 | Alvarado et al. |
| 6,530,951 | B1 | 3/2003 | Bates et al. |
| 6,537,589 | B1 | 3/2003 | Chae et al. |
| 6,539,607 | B1 | 4/2003 | Fehring et al. |
| 6,540,776 | B2 | 4/2003 | Sanders Millare et al. |
| 6,540,777 | B2 | 4/2003 | Stenzel |
| 6,544,223 | B1 | 4/2003 | Kokish |
| 6,544,543 | B1 | 4/2003 | Mandrusov et al. |
| 6,544,582 | B1 | 4/2003 | Yoe |
| 6,554,758 | B2 | 4/2003 | Turnlund et al. |
| 6,554,854 | B1 | 4/2003 | Flanagan |
| 6,555,059 | B1 | 4/2003 | Myrick et al. |
| 6,555,157 | B1 | 4/2003 | Hossainy |
| 6,558,733 | B1 | 5/2003 | Hossainy et al. |
| 6,562,136 | B1 | 5/2003 | Chappa et al. |
| 6,565,599 | B1 | 5/2003 | Hong et al. |
| 6,565,659 | B1 | 5/2003 | Pacetti et al. |
| 6,569,191 | B1 | 5/2003 | Hogan |
| 6,569,193 | B1 | 5/2003 | Cox et al. |
| 6,572,644 | B1 | 6/2003 | Moein |
| 6,572,672 | B2 | 6/2003 | Yadav et al. |
| 6,574,851 | B1 | 6/2003 | Mirizzi |
| 6,582,417 | B1 | 6/2003 | Ledesma et al. |
| 6,585,755 | B2 | 7/2003 | Jackson et al. |
| 6,585,765 | B1 | 7/2003 | Hossainy et al. |
| 6,585,926 | B1 | 7/2003 | Mirzaee |
| 6,592,614 | B2 | 7/2003 | Lenker et al. |
| 6,592,617 | B2 | 7/2003 | Thompson |
| 6,596,296 | B1 | 7/2003 | Nelson et al. |
| 6,605,114 | B1 | 8/2003 | Yan et al. |
| 6,605,154 | B1 | 8/2003 | Villareal |
| 6,605,874 | B2 | 8/2003 | Leu et al. |
| 6,610,087 | B1 | 8/2003 | Zarbatany et al. |
| 6,613,072 | B2 | 9/2003 | Lau et al. |
| 6,613,432 | B2 | 9/2003 | Zamora et al. |
| 6,616,765 | B1 | 9/2003 | Hossaony et al. |
| 6,620,617 | B2 | 9/2003 | Mathiowitz et al. |
| 6,623,448 | B2 | 9/2003 | Slater |
| 6,625,486 | B2 | 9/2003 | Lundkvist et al. |
| 6,626,939 | B1 | 9/2003 | Burnside et al. |
| 6,635,269 | B1 | 10/2003 | Jennissen |
| 6,635,964 | B1 | 10/2003 | Maex et al. |
| 6,641,611 | B2 | 11/2003 | Jayaraman |
| 6,645,135 | B1 | 11/2003 | Bhat |
| 6,645,195 | B1 | 11/2003 | Bhat et al. |
| 6,645,243 | B2 | 11/2003 | Vallana et al. |
| 6,645,547 | B1 | 11/2003 | Shekalim et al. |
| 6,656,162 | B2 | 12/2003 | Santini, Jr. et al. |
| 6,656,216 | B1 | 12/2003 | Hossainy et al. |
| 6,656,506 | B1 | 12/2003 | Wu et al. |
| 6,660,034 | B1 | 12/2003 | Mandrusov et al. |
| 6,660,381 | B2 | 12/2003 | Halas et al. |
| 6,663,662 | B2 | 12/2003 | Pacetti et al. |
| 6,663,880 | B1 | 12/2003 | Roorda et al. |
| 6,664,187 | B1 | 12/2003 | Ngo et al. |
| 6,664,335 | B2 | 12/2003 | Krishnan |
| 6,666,214 | B2 | 12/2003 | Canham |
| 6,666,880 | B1 | 12/2003 | Chiu et al. |
| 6,667,049 | B2 | 12/2003 | Janas et al. |
| 6,669,723 | B2 | 12/2003 | Killion et al. |
| 6,669,980 | B2 | 12/2003 | Hansen |
| 6,673,154 | B1 | 1/2004 | Pacetti et al. |
| 6,673,385 | B1 | 1/2004 | Ding et al. |
| 6,676,697 | B1 | 1/2004 | Richter |
| 6,676,700 | B1 | 1/2004 | Jacobs et al. |
| 6,679,980 | B1 | 1/2004 | Andreacchi |
| 6,685,986 | B2 | 2/2004 | Oldenburg et al. |
| 6,689,099 | B2 | 2/2004 | Mirzaee |
| 6,689,350 | B2 | 2/2004 | Uhrich |
| 6,689,375 | B1 | 2/2004 | Wahlig et al. |
| 6,695,920 | B1 | 2/2004 | Pacetti et al. |
| 6,699,281 | B2 | 3/2004 | Vallana et al. |
| 6,699,724 | B1 | 3/2004 | West et al. |
| 6,703,307 | B2 | 3/2004 | Lopatin et al. |
| 6,706,013 | B1 | 3/2004 | Bhat et al. |
| 6,706,273 | B1 | 3/2004 | Roessler |
| 6,709,379 | B1 | 3/2004 | Brandau et al. |
| 6,709,514 | B1 | 3/2004 | Hossainy |
| 6,712,845 | B2 | 3/2004 | Hossainy |
| 6,713,119 | B2 | 3/2004 | Hossainy et al. |
| 6,716,444 | B1 | 4/2004 | Castro et al. |
| 6,719,934 | B2 | 4/2004 | Stinson |
| 6,719,989 | B1 | 4/2004 | Matsushima et al. |
| 6,720,402 | B2 | 4/2004 | Langer et al. |
| 6,723,120 | B2 | 4/2004 | Yan |
| 6,730,064 | B2 | 5/2004 | Ragheb et al. |
| 6,733,768 | B2 | 5/2004 | Hossainy et al. |
| 6,740,040 | B1 | 5/2004 | Mandrusov et al. |
| 6,743,462 | B1 | 6/2004 | Pacetti |
| 6,746,773 | B2 | 6/2004 | Llanos et al. |
| 6,749,626 | B1 | 6/2004 | Bhat et al. |
| 6,752,826 | B2 | 6/2004 | Holloway et al. |
| 6,753,007 | B2 | 6/2004 | Haggard et al. |
| 6,753,071 | B1 | 6/2004 | Pacetti |
| 6,758,859 | B1 | 7/2004 | Dang et al. |
| 6,759,054 | B2 | 7/2004 | Chen et al. |
| 6,764,505 | B1 | 7/2004 | Hossainy et al. |
| 6,774,278 | B1 | 8/2004 | Ragheb et al. |
| 6,776,792 | B1 | 8/2004 | Yan et al. |
| 6,776,796 | B2 | 8/2004 | Falotico et al. |
| 6,780,424 | B2 | 8/2004 | Claude |
| 6,783,793 | B1 | 8/2004 | Hossainy et al. |
| 6,790,228 | B2 | 9/2004 | Hossainy et al. |
| 6,818,063 | B1 | 11/2004 | Kerrigan |
| 6,824,559 | B2 | 11/2004 | Michal |
| 6,846,323 | B2 | 1/2005 | Yip et al. |
| 6,860,946 | B2 | 3/2005 | Hossainy et al. |
| 6,861,088 | B2 | 3/2005 | Weber et al. |
| 6,865,810 | B2 | 3/2005 | Stinson |
| 6,869,443 | B2 | 3/2005 | Buscemi et al. |
| 6,878,160 | B2 | 4/2005 | Gilligan et al. |
| 6,887,270 | B2 | 5/2005 | Miller et al. |
| 6,887,485 | B2 | 5/2005 | Fitzhugh et al. |
| 6,890,546 | B2 | 5/2005 | Mollison et al. |
| 6,890,583 | B2 | 5/2005 | Chudzik et al. |
| 6,899,731 | B2 | 5/2005 | Li et al. |
| 7,008,667 | B2 | 3/2006 | Chudzik et al. |
| 2001/0007083 | A1 | 7/2001 | Roorda |
| 2001/0014717 | A1 | 8/2001 | Hossainy et al. |
| 2001/0016753 | A1 | 8/2001 | Caprio et al. |
| 2001/0020011 | A1 | 9/2001 | Mathiowitz et al. |
| 2001/0029351 | A1 | 10/2001 | Falotico et al. |
| 2001/0037145 | A1 | 11/2001 | Guruwaiya et al. |
| 2001/0044652 | A1 | 11/2001 | Moore |
| 2001/0051608 | A1 | 12/2001 | Mathiowitz et al. |
| 2002/0002399 | A1 | 1/2002 | Huxel et al. |
| 2002/0004060 | A1 | 1/2002 | Heublein et al. |
| 2002/0004101 | A1 | 1/2002 | Ding et al. |
| 2002/0005206 | A1 | 1/2002 | Falotico et al. |
| 2002/0007213 | A1 | 1/2002 | Falotico et al. |
| 2002/0007214 | A1 | 1/2002 | Falotico |
| 2002/0007215 | A1 | 1/2002 | Falotico et al. |
| 2002/0009604 | A1 | 1/2002 | Zamora et al. |
| 2002/0016625 | A1 | 2/2002 | Falotico et al. |
| 2002/0032414 | A1 | 3/2002 | Ragheb et al. |
| 2002/0032434 | A1 | 3/2002 | Chudzik et al. |
| 2002/0051730 | A1 | 5/2002 | Bodnar et al. |
| 2002/0061363 | A1 | 5/2002 | Halas et al. |
| 2002/0062148 | A1 | 5/2002 | Hart |
| 2002/0065553 | A1 | 5/2002 | Weber |
| 2002/0071822 | A1 | 6/2002 | Uhrich |
| 2002/0077693 | A1 | 6/2002 | Barclay et al. |
| 2002/0082679 | A1 | 6/2002 | Sirhan et al. |
| 2002/0087123 | A1 | 7/2002 | Hossainy et al. |
| 2002/0091433 | A1 | 7/2002 | Ding et al. |
| 2002/0094440 | A1 | 7/2002 | Llanos et al. |
| 2002/0103517 | A1* | 8/2002 | West et al. .......... 607/88 |
| 2002/0111590 | A1 | 8/2002 | Davila et al. |
| 2002/0116050 | A1 | 8/2002 | Kocur |
| 2002/0120326 | A1 | 8/2002 | Michal |
| 2002/0132045 | A1 | 9/2002 | Halas et al. |
| 2002/0138133 | A1 | 9/2002 | Lenz et al. |
| 2002/0142039 | A1 | 10/2002 | Claude |
| 2002/0155212 | A1 | 10/2002 | Hossainy |
| 2002/0161114 | A1 | 10/2002 | Gunatillake et al. |
| 2002/0165608 | A1 | 11/2002 | Llanos et al. |

| | | |
|---|---|---|
| 2002/0176849 A1 | 11/2002 | Slepian |
| 2002/0183581 A1 | 12/2002 | Yoe et al. |
| 2002/0187347 A1 | 12/2002 | Halas |
| 2002/0187632 A1 | 12/2002 | Marsh |
| 2002/0188037 A1 | 12/2002 | Chudzik et al. |
| 2002/0188277 A1 | 12/2002 | Roorda et al. |
| 2003/0003221 A1 | 1/2003 | Zhong et al. |
| 2003/0004141 A1 | 1/2003 | Brown |
| 2003/0028243 A1 | 2/2003 | Bates et al. |
| 2003/0028244 A1 | 2/2003 | Bates et al. |
| 2003/0031780 A1 | 2/2003 | Chudzik et al. |
| 2003/0032767 A1 | 2/2003 | Tada et al. |
| 2003/0033001 A1 | 2/2003 | Igaki |
| 2003/0036794 A1 | 2/2003 | Ragheb et al. |
| 2003/0039689 A1 | 2/2003 | Chen et al. |
| 2003/0040712 A1 | 2/2003 | Ray et al. |
| 2003/0040790 A1 | 2/2003 | Furst |
| 2003/0054090 A1 | 3/2003 | Hansen |
| 2003/0055482 A1 | 3/2003 | Schwager et al. |
| 2003/0059520 A1 | 3/2003 | Chen et al. |
| 2003/0060877 A1 | 3/2003 | Falotico et al. |
| 2003/0065377 A1 | 4/2003 | Davila et al. |
| 2003/0072868 A1 | 4/2003 | Harish et al. |
| 2003/0073961 A1 | 4/2003 | Happ |
| 2003/0083646 A1 | 5/2003 | Sirhan et al. |
| 2003/0083739 A1 | 5/2003 | Cafferata |
| 2003/0088307 A1 | 5/2003 | Shulze et al. |
| 2003/0093107 A1 | 5/2003 | Parsonage et al. |
| 2003/0097088 A1 | 5/2003 | Pacetti |
| 2003/0097173 A1 | 5/2003 | Dutta |
| 2003/0099712 A1 | 5/2003 | Jayaraman |
| 2003/0100865 A1 | 5/2003 | Santini, Jr. et al. |
| 2003/0105518 A1 | 6/2003 | Dutta |
| 2003/0105530 A1 | 6/2003 | Pirhonen |
| 2003/0113439 A1 | 6/2003 | Pacetti et al. |
| 2003/0113445 A1 | 6/2003 | Martin |
| 2003/0113807 A1* | 6/2003 | Berg et al. .................. 435/7.2 |
| 2003/0138487 A1 | 7/2003 | Hogan et al. |
| 2003/0150380 A1 | 8/2003 | Yoe |
| 2003/0152517 A1* | 8/2003 | Peyman .................. 424/9.6 |
| 2003/0157241 A1 | 8/2003 | Hossainy et al. |
| 2003/0158517 A1 | 8/2003 | Kokish |
| 2003/0164064 A1 | 9/2003 | Halas et al. |
| 2003/0171053 A1 | 9/2003 | Sanders |
| 2003/0185964 A1 | 10/2003 | Weber et al. |
| 2003/0187495 A1 | 10/2003 | Cully et al. |
| 2003/0190406 A1 | 10/2003 | Hossainy et al. |
| 2003/0203617 A1 | 10/2003 | Lane et al. |
| 2003/0207020 A1 | 11/2003 | Villareal |
| 2003/0208259 A1 | 11/2003 | Penhasi |
| 2003/0209835 A1 | 11/2003 | Chun et al. |
| 2003/0211230 A1 | 11/2003 | Pacetti et al. |
| 2003/0226833 A1 | 12/2003 | Shapovalov et al. |
| 2003/0236565 A1 | 12/2003 | DiMatteo et al. |
| 2004/0018296 A1 | 1/2004 | Castro et al. |
| 2004/0029952 A1 | 2/2004 | Chen et al. |
| 2004/0047978 A1 | 3/2004 | Hossainy et al. |
| 2004/0047980 A1 | 3/2004 | Pacetti et al. |
| 2004/0052858 A1 | 3/2004 | Wu et al. |
| 2004/0052859 A1 | 3/2004 | Wu et al. |
| 2004/0054104 A1 | 3/2004 | Pacetti |
| 2004/0060508 A1 | 4/2004 | Pacetti et al. |
| 2004/0062853 A1 | 4/2004 | Pacetti et al. |
| 2004/0063805 A1 | 4/2004 | Pacetti et al. |
| 2004/0071861 A1 | 4/2004 | Mandrusov et al. |
| 2004/0072922 A1 | 4/2004 | Hossainy et al. |
| 2004/0073298 A1 | 4/2004 | Hossainy |
| 2004/0086542 A1 | 5/2004 | Hossainy et al. |
| 2004/0086550 A1 | 5/2004 | Roorda et al. |
| 2004/0093077 A1 | 5/2004 | White et al. |
| 2004/0096504 A1 | 5/2004 | Michal |
| 2004/0098095 A1 | 5/2004 | Burnside et al. |
| 2004/0098117 A1 | 5/2004 | Hossainy et al. |
| 2004/0098120 A1* | 5/2004 | Williams et al. .............. 623/1.46 |
| 2004/0111149 A1 | 6/2004 | Stinson |
| 2004/0127970 A1 | 7/2004 | Saunders |
| 2004/0142015 A1 | 7/2004 | Hossainy et al. |
| 2004/0143317 A1 | 7/2004 | Stinson et al. |
| 2004/0167610 A1 | 8/2004 | Fleming, III |
| 2004/0213893 A1 | 10/2004 | Boulais |
| 2004/0236417 A1 | 11/2004 | Yan et al. |
| 2004/0265475 A1 | 12/2004 | Hossainy |
| 2005/0037052 A1 | 2/2005 | Udipi et al. |
| 2005/0038134 A1 | 2/2005 | Loomis et al. |
| 2005/0038497 A1 | 2/2005 | Neuendorf et al. |
| 2005/0043786 A1 | 2/2005 | Chu et al. |
| 2005/0049693 A1 | 3/2005 | Walker |
| 2005/0049694 A1 | 3/2005 | Neary |
| 2005/0054774 A1 | 3/2005 | Kangas |
| 2005/0055044 A1 | 3/2005 | Kangas |
| 2005/0055078 A1 | 3/2005 | Campbell |
| 2005/0056118 A1 | 3/2005 | Xia et al. |
| 2005/0058603 A1* | 3/2005 | Gao et al. .................. 424/9.32 |
| 2005/0060020 A1 | 3/2005 | Jenson |
| 2005/0064088 A1 | 3/2005 | Fredrickson |
| 2005/0065501 A1 | 3/2005 | Wallace |
| 2005/0065545 A1 | 3/2005 | Wallace |
| 2005/0065593 A1 | 3/2005 | Chu et al. |
| 2005/0074406 A1 | 4/2005 | Couvillon, Jr. et al. |
| 2005/0074545 A1 | 4/2005 | Thomas |
| 2005/0075714 A1 | 4/2005 | Cheng et al. |
| 2005/0079274 A1 | 4/2005 | Palasis et al. |
| 2005/0084515 A1 | 4/2005 | Udipi et al. |
| 2005/0106210 A1 | 5/2005 | Ding et al. |
| 2005/0113903 A1 | 5/2005 | Rosenthal et al. |

FOREIGN PATENT DOCUMENTS

| | | |
|---|---|---|
| CA | 2 007 648 | 4/1991 |
| CA | 1 322 628 | 10/1993 |
| CA | 1 336 319 | 7/1995 |
| CA | 1 338 303 | 5/1996 |
| DE | 042 24 401 | 1/1994 |
| DE | 044 07 079 | 9/1994 |
| DE | 197 31 021 | 1/1999 |
| DE | 199 16 086 | 10/1999 |
| DE | 198 56 983 | 12/1999 |
| EP | 0 108 171 | 5/1984 |
| EP | 0 144 534 | 6/1985 |
| EP | 0 301 856 | 2/1989 |
| EP | 0 380 668 | 4/1989 |
| EP | 0 351 314 | 1/1990 |
| EP | 0 364 787 | 4/1990 |
| EP | 0 396 429 | 11/1990 |
| EP | 0 397 500 | 11/1990 |
| EP | 0 464 755 | 1/1992 |
| EP | 0 493 788 | 7/1992 |
| EP | 0 526 606 | 9/1992 |
| EP | 0 514 406 | 11/1992 |
| EP | 0 517 075 | 12/1992 |
| EP | 0 540 290 | 5/1993 |
| EP | 0 553 960 | 8/1993 |
| EP | 0 554 082 | 8/1993 |
| EP | 0 565 251 | 10/1993 |
| EP | 0 578 998 | 1/1994 |
| EP | 0 604 022 | 6/1994 |
| EP | 0 621 017 | 10/1994 |
| EP | 0 623 354 | 11/1994 |
| EP | 0 627 226 | 12/1994 |
| EP | 0 649 637 | 4/1995 |
| EP | 0 665 023 | 8/1995 |
| EP | 0 701 802 | 3/1996 |
| EP | 0 701 803 | 3/1996 |
| EP | 0 709 068 | 5/1996 |
| EP | 0 716 836 | 6/1996 |
| EP | 0 732 087 | 9/1996 |
| EP | 0 832 618 | 9/1996 |
| EP | 0 756 853 | 2/1997 |
| EP | 0 809 999 | 12/1997 |
| EP | 0 832 655 | 4/1998 |
| EP | 0 834 293 | 4/1998 |
| EP | 0 850 604 | 7/1998 |
| EP | 0 850 651 | 7/1998 |
| EP | 0 879 595 | 11/1998 |
| EP | 0 910 584 | 4/1999 |
| EP | 0 923 953 | 6/1999 |
| EP | 0 953 320 | 11/1999 |
| EP | 0 970 711 | 1/2000 |
| EP | 0 972 498 | 1/2000 |

| | | |
|---|---|---|
| EP | 0 974 315 | 1/2000 |
| EP | 0 982 041 | 3/2000 |
| EP | 1 023 879 | 8/2000 |
| EP | 1 034 752 | 9/2000 |
| EP | 1 075 838 | 2/2001 |
| EP | 1 103 234 | 5/2001 |
| EP | 1 192 957 | 4/2002 |
| EP | 1 273 314 | 1/2003 |
| EP | 0 869 847 | 3/2003 |
| EP | 0 941 072 | 1/2004 |
| FR | 2 753 907 | 4/1998 |
| GB | 2 247 696 | 3/1992 |
| GB | 2 316 086 | 1/2000 |
| GB | 2 316 342 | 1/2000 |
| GB | 2 333 975 | 1/2000 |
| GB | 2 336 551 | 1/2000 |
| GB | 2 356 586 | 5/2001 |
| GB | 2 356 587 | 5/2001 |
| GB | 2 333 474 | 6/2001 |
| GB | 2 334 685 | 6/2001 |
| GB | 2 356 585 | 7/2001 |
| GB | 2 374 302 | 8/2001 |
| GB | 2 370 243 | 6/2002 |
| GB | 2 384 199 | 7/2003 |
| JP | SHO49-48336 | 12/1974 |
| JP | SHO54-18310 | 7/1979 |
| JP | SHO60-28504 | 7/1985 |
| JP | 21199867 | 5/1994 |
| JP | HEI8-33718 | 2/1996 |
| JP | HEI10-151190 | 6/1998 |
| JP | 2919971 B2 | 7/1999 |
| JP | 2001-190687 | 7/2001 |
| SU | 0872531 | 10/1981 |
| SU | 0876663 | 10/1981 |
| SU | 0905228 | 2/1982 |
| SU | 0790725 | 2/1983 |
| SU | 1016314 | 5/1983 |
| SU | 0811750 | 9/1983 |
| SU | 1293518 | 2/1987 |
| SU | 1477423 | 5/1989 |
| WO | WO 89/03232 | 4/1989 |
| WO | WO 90/01969 | 3/1990 |
| WO | WO 90/04982 | 5/1990 |
| WO | WO 90/06094 | 6/1990 |
| WO | WO 91/11176 | 8/1991 |
| WO | WO 91/12846 | 9/1991 |
| WO | WO 91/17744 | 11/1991 |
| WO | WO 91/17789 | 11/1991 |
| WO | WO 92/10218 | 6/1992 |
| WO | WO 93/06792 | 4/1993 |
| WO | WO 94/09760 | 5/1994 |
| WO | WO 94/21196 | 9/1994 |
| WO | WO 95/10989 | 4/1995 |
| WO | WO 95/11817 | 5/1995 |
| WO | WO 95/24929 | 9/1995 |
| WO | WO 95/29647 | 11/1995 |
| WO | WO 95/33422 | 12/1995 |
| WO | WO 96/28115 | 9/1996 |
| WO | WO 96/35516 | 11/1996 |
| WO | WO 96/40174 | 12/1996 |
| WO | WO 97/10011 | 3/1997 |
| WO | WO 97/45105 | 12/1997 |
| WO | WO 97/46590 | 12/1997 |
| WO | WO 98/04415 | 2/1998 |
| WO | WO 98/07390 | 2/1998 |
| WO | WO 98/08463 | 3/1998 |
| WO | WO 98/17331 | 4/1998 |
| WO | WO 98/20863 | 5/1998 |
| WO | WO 98/23228 | 6/1998 |
| WO | WO 98/32398 | 7/1998 |
| WO | WO 98/36784 | 8/1998 |
| WO | WO 99/01118 | 1/1999 |
| WO | WO 99/03515 | 1/1999 |
| WO | WO 99/16386 | 4/1999 |
| WO | WO 99/38546 | 8/1999 |
| WO | WO 99/42147 | 8/1999 |
| WO | WO 99/63981 | 12/1999 |
| WO | WO 00/02599 | 1/2000 |
| WO | WO 00/12147 | 3/2000 |
| WO | WO 00/18446 | 4/2000 |
| WO | WO 00/64506 | 11/2000 |
| WO | WO 01/01890 | 1/2001 |
| WO | WO 01/15751 | 3/2001 |
| WO | WO 01/17459 | 3/2001 |
| WO | WO 01/17577 | 3/2001 |
| WO | WO 01/43727 | 6/2001 |
| WO | WO 01/45763 | 6/2001 |
| WO | WO 01/49338 | 7/2001 |
| WO | WO 01/51027 | 7/2001 |
| WO | WO 01/52772 | 7/2001 |
| WO | WO 01/57144 | 8/2001 |
| WO | WO 01/74414 | 10/2001 |
| WO | WO 01/91918 | 12/2001 |
| WO | WO 02/03890 | 1/2002 |
| WO | WO 02/26162 | 4/2002 |
| WO | WO 02/34311 | 5/2002 |
| WO | WO 02/47731 | 6/2002 |
| WO | WO 02/49771 | 6/2002 |
| WO | WO 02/056790 | 7/2002 |
| WO | WO 02/058753 | 8/2002 |
| WO | WO 02/087550 | 11/2002 |
| WO | WO 02/102283 | 12/2002 |
| WO | WO 03/000308 | 1/2003 |
| WO | WO 03/007918 | 1/2003 |
| WO | WO 03/007919 | 1/2003 |
| WO | WO 03/022323 | 3/2003 |
| WO | WO 03/028780 | 4/2003 |
| WO | WO 03/037223 | 5/2003 |
| WO | WO 03/039612 | 5/2003 |
| WO | WO 03/061841 | 7/2003 |
| WO | WO 03/072084 | 9/2003 |
| WO | WO 03/072086 | 9/2003 |
| WO | WO 03/080147 | 10/2003 |
| WO | WO 03/082368 | 10/2003 |
| WO | WO 2004/000383 | 12/2003 |
| WO | WO 2004/009145 | 1/2004 |
| WO | WO 2004/017947 | 3/2004 |
| WO | WO 2004/017976 | 3/2004 |
| WO | WO 2004/023985 | 3/2004 |
| WO | WO 2004/024339 | 3/2004 |
| WO | WO 2005/044224 | 5/2005 |

OTHER PUBLICATIONS

A Boulay, J Rudloff, J Ye, S Zumstein-Mecker, T O'Reilly, DB Evans, S Chen, HA Lane. "Dual Inhibition of mTOR and Estrogen Receptor Signaling In vitro Induces Cell Death in Models of Breast Cancer." Clin Cancer Res 2005;11(14). 5319-5328. Jul. 15, 2005.*

A Panwalkar, S Verstovsek, FJ Giles. "Mammalian Target of Rapamycin As Therapy for Hematologic Malignancies." Cancer, Feb. 15, 2004, vol. 100 No. 4, pp. 657-666.*

LR Hirsch. "Diagnostic and Therapeutic Applications of Metal Nanoshells." Rice University, Ph.D Thesis. Mar. 2004, 112 pages.*

GF Paciotti, L Myer, D Weinreich, D Goia, N Pavel, RE McLaughlin, L Tamarkin. "Colloidal Gold: A Novel Nanoparticle Vector for Tumor Directed Drug Delivery." Drug Delivery, vol. 11, 2004, pp. 169-183.*

F Matsuoka, M Shinkai, H Honda, T Kubo, T Sugita, T Kobayashi. "Hyperthermia Using Magnetite Cationic Liposomes for Hamster Osteosarcoma." BioMagnetic Research and Technology 2:3, 2004, 6 pages.*

RJ Lee, PS Low. "Folate-mediated tumor cell targeting of liposome-entrapped doxorubicin in vitro." Biochimica et Biophysica Acta, vol. 1233, 1995, pp. 134-144.*

LR Hirsch, RJ Stafford, JA Bankson, SR Sershen, B Rivera, RE Price, JD Hazle, NJ Hales, JL West. "Nanoshell-mediated near-infrared thermal therapy of tumors under magnetic resonance guidance." PNAS, vol. 100, No. 23, Nov. 11, 2003, pp. 13549-13554.*

JF Hainfeld, FR Furuya, RD Powell. "Metallosomes." Journal of Structural Biology, vol. 127, 1999, pp. 152-160.*

G Molema, LFMH de Leij, DKF Meijer. "Tumor Vascular Endothelium: Barrier or Target in Tumor Directed Drug Delivery and Immunotherapy." Pharmaceutical Research, vol. 14 No. 1, 1997, pp. 2-10.*

SS Patel, NM Patel, MR Patel. "Liposome: A Versatile Platform for Targeted Delivery of Drugs." Latest Reviews, vol. 4, Issue 52006.

http://www.pharmainfo.net/reviews/liposome-versatile-platform-targeted-delivery-drugs, Sep. 8, 2006, 15 printed pages.*

N. Yagi, Y Ogawa, M Kodaka, T Okada, T Tomohiro, T Konakahara, H Okuno. "Preparation of Functional Liposomes with Peptide Ligands and Their Binding to Cell Membranes." Lipids, vol. 35 No. 6, 2000, pp. 673-680.*

International Search Report for application PCT/US2007/014079, mailed Jul. 21, 2008, 20 pgs.

Remita et al., "Radiation induced synthesis of silver nanoshells formed onto organic micelles", Eur. Phys. J. D 34, pp. 231-233 (2005).

U.S. Appl. No. 10/255,913, filed Sep. 26, 2002, Tang et al.
U.S. Appl. No. 10/304,669, filed Nov. 25, 2002, Madriaga et al.
U.S. Appl. No. 10/317,435, filed Dec. 11, 2002, Hossainy et al.
U.S. Appl. No. 10/322,255, filed Dec. 17, 2002, Chen et al.
U.S. Appl. No. 10/409,410, filed Apr. 7, 2003, Pacetti.
U.S. Appl. No. 10/439,415, filed May 15, 2003, Perng.
U.S. Appl. No. 10/602,487, filed Jun. 23, 2003, Castro et al.
U.S. Appl. No. 10/630,250, filed Jul. 30, 2003, Pacetti et al.
U.S. Appl. No. 10/676,545, filed Sep. 30, 2003, Fox et al.
U.S. Appl. No. 10/680,905, filed Oct. 7, 2003, Pacetti et al.
U.S. Appl. No. 10/738,704, filed Dec. 16, 2003, Pacetti et al.
U.S. Appl. No. 10/741,214, filed Dec. 19, 2003, Pacetti.
U.S. Appl. No. 10/747,996, filed Dec. 29, 2003, Chen et al.
U.S. Appl. No. 10/750,139, filed Dec. 30, 2003, DesNoyer et al.
U.S. Appl. No. 10/805,036, filed Mar. 16, 2004, Pacetti.
U.S. Appl. No. 10/816,072, filed Mar. 31, 2004, Dugan et al.
U.S. Appl. No. 10/824,754, filed Apr. 15, 2004, Perng.
U.S. Appl. No. 10/833,902, filed Apr. 27, 2004, Chen et al.
U.S. Appl. No. 10/835,229, filed Apr. 28, 2004, Prabhu et al.
U.S. Appl. No. 10/835,656, filed Apr. 30, 2004, Tang et al.
U.S. Appl. No. 10/851,411, filed May 20, 2004, Chen.
U.S. Appl. No. 10/855,294, filed May 26, 2004, Pacetti et al.
U.S. Appl. No. 10/877,527, filed Jun. 24, 2004, Yan et al.
U.S. Appl. No. 10/897,244, filed Jul. 21, 2004, Hossainy et al.
U.S. Appl. No. 10/928,587, filed Aug. 26, 2004, Hossainy et al.
U.S. Appl. No. 10/931,853, filed Aug. 31, 2004, Hossainy et al.
U.S. Appl. No. 10/932,364, filed Aug. 31, 2004, Foreman et al.
U.S. Appl. No. 11/015,313, filed Dec. 16, 2004, Pacetti et al.
U.S. Appl. No. 11/093,166, filed Mar. 28, 2005, Kerrigan.
U.S. Appl. No. 11/115,631, filed Apr. 26, 2005, Chen.
U.S. Appl. No. 11/119,020, filed Apr. 29, 2005, Hossainy et al.
U.S. Appl. No. 11/187,467, filed Jul. 22, 2005, Desnoyer et al.
U.S. Appl. No. 11/453,704, filed Jun. 14, 2006, Ludwig et al.
U.S. Appl. No. 11/473,822, filed Jun. 23, 2006, Ludwig et al.

Angioplasty.org., *Balloons and Stents*, http://www.ptca.ord/devices04.html, printed Oct. 15, 2004, 2 pages.

Anonymous, *Bioabsorbable stent mounted on a catheter having optical coherence tomography capabilities*, Research Disclosure, pp. 1159-1162 (Sep. 2004).

Anonymous, *Capillary Action*, http://www.ndt-ed.ord/EducationResources/CommunityCollege/PenetrantTest/Introduction/Keywords/pt1.htm, printed Aug. 12, 2005, 1 page.

Anonymous, *Capillary Force Lithography (CFL)*, Nano Processing and Organic Devices Lab, 2 pages (no date).

Anonymous, *Capillary Rise of Liquid in Different Vanes Under Variable Residual Acceleration*, http://www.zarm.uni-bremen.de/2forschund/drenzph/isoterm/cap_rise/kapst_en.htm, ZARM—University of Bremen, printed Jun. 25, 2003, 2 pages.

Anonymous, *Cardiologists Draw—Up The Dream Stent*, Clinica 710, pp. 15 (Jun. 17, 1996), http://wvvw.dialogweb.com/cgi/document?reg=1061848202959, printed Aug. 25, 2003, 2 pages.

Anonymous, *Coating Techniques, Air Knife Coating*, http://www.ferron-magnetic.co.uk/coatings/airknife.htm, printed Jul. 1, 2003, 1 page.

Anonymous, *Coating Techniques, Gap Coating (Knife Over Roll, etc.)*, http://www.ferron-magnetic.co.uk/coatings/knife.htm, printed Jul. 1, 2003, 1 page.

Anonymous, *Coating Techniques, Gravure Coating*, http://www.ferron-magnetic.co.uk/coatings/gravure.htm, printed Jul. 1, 2003, 2 pages.

Anonymous, *Coating Techniques, Reverse Roll Coating*, http://www.ferron-magnetic.co.uk/coatings/revroll.htm, printed Jul. 1, 2003, 22 pages.

Anonymous, *Heparin-coated stents cut complications By 30%*, Clinica 732, pp. 17 (Nov. 18, 1996), http://www.dialogweb.com/cgi/document?reg=1061847871753, printed Aug. 25, 2003, 2 pages.

Anonymous, *Liquid Gravity Motor*, http://w ww.drspark86.com/idea001.html, printed Jun. 24, 2003, 2 pages (no date).

Anonymous, *Porosimetry—Why characterize the porosity?* 42 pages (no date.).

Anonymous, *Rolling Therapeutic Agent Loading Device for Therapeutic Agent Delivery or Coated Stent* (Abstract 434009), Res. Disclos. pp. 974-975 (Jun. 2000).

Anonymous, *Stenting Continues to Dominate Cardiology*, http://www.dialogweb.com/cdi/document?reg=1061848017752, Clinica vol. 720, pp. 22 (Sep. 2, 1996), printed Aug. 25, 2003, 2 pages.

Anonymous, *Surface Energy (Surface Wetting Capability)*, http://www.ndt-ed.org/EducationResources/CommunityCollege/PenetrantTest/PTMaterials/surfaceenergy.htm, printed Apr. 6, 2004, 3 pages (no date).

Anonymous, *The 14$^{th}$ International Young Physicists Tournament, The winning report*, Research Center for Quantum Information, Slovak Academy of Sciences, 5 pages (no date).

Anonymous, *The Wicking Well System*, http://www.decorative.com/wicking.html, printed Jun. 24, 2003, 1 page.

Anonymous, *Typical Parylene Properties*, 3 pages (no date).

Anonymous, *Viscosity*, Commonwealth of Australia, 7 pages (no date).

Albericio et al., *On the Use of PyAOP, a phosphonium salt derived from HOAt, in Solid-Phase Peptide Synthesis*, Tetrahedron Letters vol. 38, pp. 4853-4856 (1997).

Ansari, *End-to-End Tubal Anastomosis Using an Absorbable Stent*, Fertility and Sterility, vol. 32, No. 2, pp. 197-201 (Aug. 1979).

Ansari, *Tubal Reanastomosis Using Absorbable Stent*, International Journal of Fertility, vol. 23, No. 4, pp. 242-243 (1978).

Aoyagi et al., *Preparation of cross-linked aliphatic polyester and application to thermo-responsive material*, Journal of Controlled Release 32, pp. 87-96 (1994).

Barath et al., *Low Dose of Antitumor Agents Prevents Smooth Muscle Cell Proliferation After Endothelial Injury*, JACC vol. 3, No. 2, pp. 252A (Feb. 1989).

Barbucci et al., *Coating of commercially available materials with a new heparinizable.Material*, Journal of Biomedical Materials Research, vol. 25, pp. 1259-1274 (1991).

Beach et al., *Xylylene Polymers*, Encyclopedia of Polymer Science and Engineering, vol. 17, 2nd Edition, pp. 990-1025 (1989).

Boston Scientific, *Express $^{2TM}$ Coronary Stent System*, http://www.bostonscientific.com/med_specialty/deviceDetail.jsp?task=tskBasicDevice.jsp&sectionId=4&relId=2,74,75,76&deviceId=11001&uniqueId=MPDB1180&clickType=endeca, printed Aug. 8, 2005, 1 page.

Bull, *Parylene Coating for Medical Applications*, Medical Product Manufacturing News, 2 pages (Mar. 1993).

Casper et al., *Fiber-Reinforced Absorbable Composite for Orthopedic Surgery*, Polymeric Materials Science and Engineering, vol. 53, pp. 497-501(1985).

Charlson et al., *Temperature Selective Deposition of Parylene-C*, IEEE Transactions of Biomedical Engineering, vol. 39, No. 2, pp. 202-206 (Feb. 1992).

Chen et al., *The Kinetics of Wicking of Liquid Droplets into Yarns*, submitted to the Textile Research Journal, pp. 1-30 (Apr. 2001).

Chung et al., *Inner core segment design for drug delivery control of thermo-responsive polymeric micelles*, Journal of Controlled Release, vol. 65, pp. 93-103 (2000).

Colombo et al., *Intracoronary Stenting Without Anticoagulation Accomplished with Intravascular Ultrasound Guidance*, Circulation vol. 91, No. 6, 1676-1688 (1995).

Crofford, *Diabetes contol and complications*, Am. Rev. Med. 46, pp. 267-279 (1995).

Crowe et al., *Absorption and Intestinal Metabolism of SDZ-RAD and Rapamycin in Rats*, Drug Metabolism and Disposition, vol. 27, No. 5, pp. 627-632 (1999).

De Scheerder et al., *Biocompatibility of polymer-coated oversized metallic stents implanted in normal porcine coronary arteries*, Atherosclerosis, vol. 114, pp. 105-114 (1995).

Detweiler et al., *Gastrointestinal Sutureless Anastomosis Using Fibrin Glue: Reinforcement of the Sliding Absorbable Intraluminal Nontoxic Stent and Development of a Stent Placement Device*, Journal of Investigative Surgery, vol. 9, No. 2, pp. 111-130 (Mar. /Apr. 1996).

Detweiler et al., *Sliding, Absorbable, Reinforced Ring and an Axially Driven Stent Placement Device for Sutureless Fibrin Glue Gastrointestinal Anastomisis*, Journal of Investigative Surgery, vol. 9, No. 6, pp. 495-504 (Nov./Dec. 1996).

Detweiler et al., *Sutureless Anastomosis of the Small Intestine and the Colon in Pigs Using an Absorbable Intraluminal Stent and Fibrin Glue*, Journal of Investigative Surgery, vol. 8, No. 2, pp. 129-140 (Mar. 1995).

Detweiler et al., *Sutureless Cholecystojejunostomy in Pigs Using an Absorbable Intraluminal Stent and Fibrin Glue*, Journal of Investigative Surgery, vol. 9, No. 1, pp. 13-26 (Jan./Feb. 1996).

Dev et al., *Kinetics of Drug Delivery to the Arterial Wall Via Polyurethane-Coated Removable Nitinol Stent: Comparative Study of Two Drugs*, Catheterization and Cardiovascular Diagnosis, vol. 34, pp. 272-278 (1995).

Devanathan et al., *Polymeric Conformal Coatings for Implantable Electronic Devices*, IEEE Transactions on Biomedical Engineering, vol. BME-27, No. 11, pp. 671-675 (1980).

Dichek et al., *Seeding of Intravascular Stents with Genetically Engineered Endothelial Cells*, Circulation, vol. 80, No. 5, pp. 1347-1353 (Nov. 1989).

Dong et al., *Thermally Reversible Hydrogels: III. Immobilization of Enzymes for Feedback Reaction Control*, J. of Controlled Release 4, pp. 223-227 (1986).

Dreyer et al., *Critical Velocities in Open Capillary Flows*, pp. 604-609 (no date).

Duerig et al., *A comparison of balloon-and self-expanding stents*, Min. Invas. Ther. & Allied Technol., vol. 11, No. 4, pp. 173-178 (2002).

Dutkiewicz, *Some Advances in Nonwoven Structures for Absorbency, Comfort and Aesthetics*, AUTEX Research Journal, vol. 2, No. 3, pp. 153-165 (Sep. 2002).

EFD, *780S Series Spray Valves VALVEMATE™ 7040 Controller Operating Manual*, 24 pages (2002).

Eigler et al., *Local Arterial Wall Drug Delivery from a Polymer Coated Removable Metallic Stent: Kinetics, Distribution, and Bioactivity of Forskolin*, JACC, vol. 4A, pp. 701-701, Abstract (Feb. 1994).

Elbert et al., *Conjugate Addition Reactions Combined with Free-Radical Cross-Linking for the Design of Materials for Tissue Engineering*, Biomacromolecules, vol. 2, pp. 430-441 (2001).

Erickson et al., *Numerical Simulations of Capillary-Driven Flows in Nonuniform Cross-Sectional Capillaries*, Journal of Colloid and Interface Science, vol. 250, pp. 422-430 (2002).

Eskin et al., *Growth of Cultured Calf Aortic Smooth Muscle Cells on Cardiovascular Prosthetic Materials*, J. Biomed. Mater. Res. vol. 10, pp. 113-122 (1976).

Eskin et al., *Tissue Cultured Cells: Potential Blood Compatible Linings for Cardiovascular Prostheses*, Polymer Science and Technology, vol. 14, pp. 143-161 (no date).

Fischell et al., *Low-Dose, β-Particle Emission from 'Stent' Wire Results in Complete, Localized Inhibition of Smooth Muscle Cell Proliferation*, Circulation, vol. 90, No. 6, pp. 2956-2963 (Dec. 1994).

Fischell et al., *The Bx VELOCITY™ Stent*, 5 pages, Biocompatibles Ltd. (2001).

Gengenbach et al., *Evolution of the Surface Composition and Topography of Perflurinated Polymers Following Ammonia-Plasma Treatment*, Plasma Surface Modifications of Polymers, pp. 123-146 (1994).

Gercken et al., *Results of the Jostent Coronary Stent Graft Implantation in Various Clinical Settings: Procedural and Follow-Up Results*, vol. 56, No. 3, pp. 353-360 (2002).

Ginsberg-Feltner, *Insulin-Dependent Diabetes Mellitus*, Pediatrics in review, vol. 11, No. 8, pp. 239-248 (1990).

Gittleman et al., *Preparation and characterization of oligosaccharide- and oligopeptide-bearing stealth liposomes*, Polym. Prepr. vol. 38 (1), p. 607 (1997).

Gölander et al., *RF-Plasma-Modified Polystyrene Surfaces for Studying Complement Activation*, J. Biomater. Sci. Plymer Edn., vol. 4, No. 1 pp. 25-30 (1992).

Guidant, *ACS Rx Multi-Link™ Coronary Stent System*, 6 pages (no date).

Guidant, *Guidant Multi-Link Vision OTW Coronary Stent System*, 2 pages (no date).

Hahn et al., *Biocompatibility of Glow-Discharge-Polmerized Films and Vacuum-Deposited Parylene*, Journal of Applied Polymer Science: Applied Polymer Symposium 38, 55-64 (1984).

Hahn et al., *Glow Discharge Polymers as Coatings for Implanted Devices*, John M. Dalton Research Center, University of Missouri-Columbia and the Graduate Center for Materials Research, pp. 109-113 (1981).

He et al., *Assessment of Tissue Blood Flow Following Small Artery Welding with an Intraluminal Dissolvable Stent*, Microsurgery, vol. 19, No. 3, pp. 148-152 (1999).

Hehrlein et al., *Low-Dose Radioactive Endovascular Stents Prevent Smooth Muscle Cell Proliferation and Neointimal Hyperplasia in Rabbits*, Circulation, vol. 92, No. 6, pp. 1570-1575 (Sep. 15, 1995).

Helmus, *Overview of Biomedical Materials*, MRS Bulletin, pp. 33-38 (Sep. 1991).

Herdeg et al., *Antiproliferative Stent Coatings: Taxol and Related Compounds*, Semin. Intervent. Cardiol., vol. 3, pp. 197-199 (1998).

Hermanson, *Bioconjugate Techniques*, Academic Press, 11 pgs. (1996).

Hirsch et al. *Nanoshell-mediated near-infrared thermal therapy of tumors under magnetic resonance guidance*, PNAS vol. 100, No. 23, pp. 13549-13554 (2003).

Hollahan et al., *Attachment of Amino Groups to Polymer Surfaces by Radiofrequency Plasmas*, Journal of Applied Polymer Science, vol. 13, pp. 807-816 (1969).

Hoffman et al., *Thermally Reversible Hydrogels: II. Delivery and Selective Removal of Substances from Aqueous Solutions*, J. of controlled Release 4, pp. 213-222 (1986).

Huang et al., *Biodegradable Polymers Derived from Aminoacids*, Macromol. Symp. 144, 7-32 (1999).

Impulse Jetting, *About Us*, http://www.impulsejetting.com/about.html, printed Dec. 18, 2000, 1 page.

Impulse Jetting, *Our Technology*, http://www.impulsejetting.com/tech1.html, printed Dec. 18, 2000, 1 page.

Inagaki et al., *Hydrophilic Surface Modification of Polyethylene by No-Plasma Treatment*, Adhesion Sci. Technol., vol. 4, No. 2, pp. 99-107 (1990).

Inoue et al., *An AB block copolymer of oligo(methyl methacrylate) and poly(acrylic acid) for micellar delivery of hydrophobic drugs*, Journal of Controlled Release, vol. 51, pp. 221-229 (1998).

International Search Report and Written Opinion of WIPO Application No. WIPO/US2004/026137 filed Aug. 11, 2004 (Jan. 31, 2005).

Itabashi et al., *Electroless Deposited CoWB for Copper Diffusion Barrier Metal*, International Interconnect Technology Conference, pp. 285-287 (2002).

John Ritchie Production Group, *Production of Stents* (presentation), 15 pages (Apr. 24, 2003).

Kataoka et al., *Block Copolymer Micelles as Vehicles for Drug Delivery*, Journal of Controlled Release vol. 24, pp. 119-132 (1993).

Katsarava et al., *Amino Acid-Based Bioanalogous Polymers. Synthesis and Study of Regular Poly(ester amide)s Based on Bis(α-amino acid)α,ω-Alkylene Diesters, and Aliphatic Dicarbolic Acids*, Journal of Polymer Science, Part A: Polymer Chemistry, vol. 37, 391-407 (1999).

Kaufman, *Diabetes Mellitus*, Pediatrics in Review, vol. 18, No. 11, pp. 383-393 (1997).

Kawai et al., *Physiologically Based Pharmacokinetics of Cyclosporine A: Extension to Tissue Distribution Kinetics in Rats and Scale-up to Human*, The Journal of Pharmacology and Experimental Therapeutics, vol. 287, No. 2, pp. 457-468 (1998).

Kelley et al., *Totally Resorbable High-Strength Composite Material*, Advances in Biomedical Polymers, vol. 35, pp. 75-85 (1987).

Klocke et al, *How Soil Holds Water* (G90-964), http://ianrpubs.unl.edu/fieldcrops/g964.htm, printed Apr. 6, 2004, 9 pages.

Konopka, *In-Plane Moisture Transport in Nonwovens*, Nonwovens Cooperative Research Center, NC State University, 56 pages (no date).

Kostarelos, *Engineering Stealth™ Liposome Surfaces: Exercise in Colloid Chemistry Principles*, NATO ASI Ser., Ser. A, vol. 300, pp. 139-145 (1998).

Kovarik et al., *Pharmacokinetic and Pharmacodynamic Assessments of HMG-CoA Reductase Inhibitors When Coadministered with Everolimus*, Journal of Clinical Pharmacology, vol. 42, pp. 222-228 (2002).

Kubies et al., *Microdomain Structure in polylactide-block-poly(ethylene oxide) copolymer films*, Biomaterials, vol. 21, pp. 529-536 (2000).

Kutryk et al., *Coronary Stenting: Current Perspectives, a companion to the Handbook of Coronary Stents*, 16 pages (1999).

Lambert et al., *Localized Arterial Wall Drug Delivery From a Polymer-Coated Removable Metallic Stent*, Circulation, vol. 90, No. 2, pp. 1003-1011 (Aug. 1994).

Lemos et al., *Coronary Restenosis After Sirolimus-Eluting Stent Implantation*, Circulation, vol. 108, No. 3, pp. 257-260 (Jul. 22, 2003).

Levy et al., *Strategies for Treating Arterial Restenosis Using Polymeric Controlled Release Implants*, Biotechnology and Bioactive Polymers, pp. 259-268 (1994).

Liermann et al., *Prophylactic Endovascular Radiotherapy to Prevent Intimal Hyperplasia after Stent Implantation in Femoropopliteal Arteries*, CardioVascular and Interventional Radiology, vol. 17, pp. 12-16 (1994).

Liu et al., *Drug Release Characteristics of Unimolecular Polymeric Micelles*, Journal of Controlled Release, vol. 68, pp. 167-174 (2000).

Loeb et al., *Parylene as a Chronically Stable, Reproducible Microelectrode Insulator*, IEEE Transactions on Biomedical Engineering, pp. 121-128 (Mar. 1977).

Loh et al., *Plasma Enhanced Parylene Deposition*, Antec, pp. 1099-1103 (1991).

Machine Solutions, *FFS700 MSI Balloon Form/Fold/Set Equipment (PTCA), FFS800 MSI Balloon Form/Fold/Set Equipment (PTA)*, http://machinesolutions.org/ffs7_8.html, printed Nov. 21, 2003 (2 pgs.).

Machine Solutions, *SC700 MSI Stent Crimping Equipment (PTCA), SC800 MSI Stent Crimping Equipment (PTA)*, http://www.machinesolutions.org/sc7_8.html, printed Nov. 21, 2003, 2 pages.

Malik et al., *Development of an Energetic Ion Assisted Mixing and Deposition Process for $TIN_x$ and Diamondlike Carbon Films, Using a Co-axial Geometry in Plasma Source Ion Implantation*, J. Vac. Sci. Technol. A, vol. 15, No. 6, pp. 2875-2879 (Nov./Dec. 1997).

Malik et al., *Overview of plasma source ion implantation research at University of Wisconsin-Madison*, J. Vac. Sci. Technol. B, No. 12, vol. 2, pp. 843-849 (Mar./Apr. 1994).

Malik et al., *Sheath dynamics and dose analysis for planar targets in plasma source ion implantation*, Plasma Sources Sci. Technol. vol. 2, pp. 81-85 (1993).

Marconi et al., *Covalent bonding of heparin to a vinyl copolymer for biomedical applications*, Biomaterials, vol. 18, No. 12, pp. 885-890 (1997).

Martin et al., *Enhancing the biological activity of immobilized osteopontin using a type-1 collagen affinity coating*, J. Biomed. Mater. Res., vol. 70A, pp. 10-19 (May 14, 2004).

Matsumaru et al., *Embolic Materials for Endovascular Treatment of Cerebral Lesions*, J. Biomater. Sci. Polymer Edn., vol. 8, No. 7, pp. 555-569 (1997).

Mauduit et al., *Hydrolytic degradation of films prepared from blends of high and low molecular weight poly(DL-lactic acid)s*, J. Biomed. Mater. Res., vol. 30, pp. 201-207 (1996).

Middleton et al., *Synthetic biodegradable polymers as orthopedic devices*, Biomaterials, vol. 21, pp. 2335-2346 (2000).

Miyazaki et al., *Antitumor Effect of Implanted Ethylene-Vinyl Alcohol Copolymer Matrices Containing Anticancer Agents on Ehrlich Ascites Carcinoma and P388 Leukemia in Mice*, Chem. Pharm. Bull., vol. 33, No. 6, pp. 2490-2498 (1985).

Miyazawa et al., *Effects of Pemirolast and Tranilast on Intimal Thickening After Arterial Injury in the Rat*, J. Cardiovasc. Pharmacol., vol. 30, No. 2, pp. 157-162 (1997).

Meissner et al., *Intravascular Optical Coherence Tomography: Comparison with Histopathology in Atherosclerotic Peripheral Artery Specimens*, Opt. Coherence Tomography vs Histopthology in Atherosclerosis vol. 17, No. 2 pp. 343-349 (2006).

Moody, *Vacuum Coating Ultrasonic Transducers*, 1 page, Sensors (Dec. 1993).

Muller et al., *Advances in Coronary Angioplasty: Endovascular Stents*, Coronary Artery Disease, vol. 1, No. 4., pp. 438-448 (Jul./Aug. 1990).

Musyanovych et al., *Grafting of Amino functional Monomer onto Initiator-Modified Polystyrene Particles*, Longmuir 2005, 21, pp. 2209-2217 (2004).

Neimark et al., *Hierarchical Pore Structure and Wetting Properties of Single-Wall Carbon Nanotube Fibers*, Nano Letters, vol. 3, No. 3, pp. 419-423 (2003).

Nichols et al., *Electrical Insulation of Implantable Devices by Composite Polymer Coatings*, ISA Transactions, vol. 26, No. 4, pp. 15-18 (1987).

Nordrehaug et al., *A Novel Biocompatible Coating Applied to Coronary Stents*, EPO Heart Journal 14, p. 321 (P1694), Abstr. Suppl. (1993).

Nova Tran™ Custom Coating Services, *Parylene Conformal Coating*, 8 pages (no date).

Ohsawa et al., *Preventive Effects of an Antiallergic Drug, Pemirolast Potassium, on Restenosis After Percutaneous Transluminal Coronary Angioplasty*, American Heart Journal, vol. 136, No. 6, pp. 1081-1087 (Dec. 1998).

Oldenburg et al., *Nanoengineering of optical resonances*, Chem. Physics Letters 288, pp. 243-247 (1998).

Oldenburg et al., *Infrared extinction properties of gold nanoshells*, Applied Physics Letters, vol. 75, No. 19, pp. 2897-2899 (1999).

Olson, *Parylene, a Biostabel Coating for Medical Applications*, Specialty Coating Systems, Inc. Nova Tran™ Parylene Coating Services (no date).

Ozaki et al., *New Stent Technologies*, Progress in Cardiovascular Diseases, vol. XXXIX, No. 2, pp. 129-140 (Sep./Oct. 1996).

Para Tech Coating Company, *Galxyl*, Parylene Coatings by Para Tech, 1 page (no date).

Para Tech Coating Company, *Lab Top® Parylene Deposition System*, 2 pages (no date).

Pechar et al., *Poly(ethylene glycol) Multiblock Copolymer as a Carrier of Anti-Cancer Drug Doxorubicin*, Bioconjucate Chemistry vol. 11, No. 2, pp. 131-139 (Mar./Apr. 2000).

Peng et al., *Role of polymers in improving the results of stenting in coronary arteries*, Biomaterial, vol. 17, pp. 685-694 (1996).

Peuster et al., *A novel approach to temporary stenting: degradable cardiovascular stents produced from corrodible metal-results 6-18 months after implantation into New Zealand white rabbits*, Heart vol. 86, pp. 563-569 (2001).

Pietrzak et al., *Bioabsorbable Fixation Devices: Status for the Craniomaxillofacial Surgeon*, Journal of Craniofacial Surgery, vol. 8, No. 2, pp. 92-96 (1997).

Pietrzak et al., *Bioresorbable Implants—Practical Considerations*, Bone, vol. 19, No. 1, Supplement, pp. 109S-119S (Jul. 1996).

Poncin-Epaillard et al., *Reactivity of a Polypropylene Surface Modified in a Nitrogen Plasma*, Plasma Surface Modification of Polymers pp. 167-180 (1994).

Prabhu, *Computational Modeling in Stent-based Drug Delivery*, Business Briefing: Medical Device Manufacturing & Technology, 4 pages (2004).

Prakash et al., *Electrophilic Modification of Polystyrene Nanospheres*, J. of Nanoscience and Nanotechnology, vol. 5, pp. 397-403 (2005).

Ramos et al., *Modeling the emulsion polymerization of amino-functionalized latex particles*, Polymer 47 pp. 1405-1413 (2006).

Ramos et al., *Polymeric and Colloidal Features of Latex Particles with surface Amino Groups Obtained by Semicontinuous Seeded Cationic Emulsion Polymerization*, J. of Polymer Science, Plymer chemistry, vol. 43, pp. 3878-3886 (2005).

Redman, *Clinical Experience with Vasovasostomy Utilizing Absorbable Intravasal Stent*, Urology, vol. XX, No. 11, pp. 59-61 (Jul. 1982).

Refracton Techonolgies, Corp., *Fine Bubble Diffusers*, 2 pages (do date).

Refracton Techonolgies, Corp., *Refractron Advanced Porous Ceramic Product Capabilities*, http://www.refractron.com/ecom/sp/cat=Product+Information, printed Apr. 6, 2004, 3 pages.

Refracton Technologies Corp., http://www.refractron.com/ecom/sp/cat=Custom+Applications, printed Jun. 24, 2003, 1 page.

Rust et al., *The Effect of Absorbable Stenting on Postoperative Stenosis of the Surgically Enlarged Maxillary Sinus Ostia in a Rabbit Animal Model*, Archives of Otolaryngology, Head and Neck Surgery, vol. 122, pp. 1395-1397 (Dec. 1996).

Sadhir et al., *The Adhesion of Glow-Discharge Polymers, Silastic And Parylene to Implantable Platinum Electrodes: Results of Tensil Pull tests After Exposure to Isotonic Sodium Chloride*, Biomaterials, vol. 2, pp. 239-243 (Oct. 1981).

Saotome, et al., *Novel Enzymatically Degradable Polymers Comprising α-Amino Acid, 1,2-Ethanediol, and Adipic Acid*, Chemistry Letters, pp. 21-24, (1991).

Schatz, *A View of Vascular Stents*, Circulation, vol. 79, No. 2, pp. 445-457 (Feb. 1989).

Scheuer et al., *Model of plasma source ion implantation in planar, cylindrical, and spherical geometries*, J. Appl. Phys., vol. 67, No. 3, pp. 1241-1245 (Feb. 1990).

Schmidt et al., *Long-term Implants of Parylene-C Coated Microelectrodes*, Medical & Biological Engineering & Computing, pp. 96-101 (Jan. 1988).

Serkova et al., *Tissue Distribution and Clinical Monitoring of the Novel Macrolide Immunosuppressant SDZ-RAD and its Metabolites in Monkey Lung Transplant Recipients: Interaction with Cyclosporine*, The Journal of Pharmacology and Experimental Therapeutics, vol. 294, No. 1, pp. 323-332 (2000).

Serruys et al., *I Like the Candy, I Hate the Wrapper; the $^{32}P$ Radioactive Stent*, Circulation, vol. 101, pp. 3-7 (Jan. 2000).

Shamim et al., *Measurement of electron emission due to energetic ion bombardment in plasma source ion implantation*, J. Appl. Phys., vol. 70, No. 9, pp. 4756-4759 (Nov. 1991).

Shamim et al., *Measurements of Spatial and Temporal Sheath Evolution for Spherical and Cylindrical Geometrics in Plasma Source Ion Implantation*, J. Appl. Phys., vol. 69, No. 5, pp. 2904-2908 (Mar. 1991).

Shigeno, *Prevention of Cerebrovascular Spasm By Bosentan, Novel Endothelin Receptor*, Chemical Abstract 125:21230 (1996).

Sono Tek Corporation, *AccuMist™ for Single Stent Coating Applications*, http://www.sono-tek.com/biomedical/accumist_stent.html, printed Aug. 2, 2005, 3 pages.

Sono Tek Corporation, *MediCoat™ DES 1000, Benchtop Stent Coating System*, http://www.sono-tek.com/biomedical/medicoat_standalone.html, printed Aug. 2, 2005, 4 pages.

Sono Tek Corporation, *MicroMist for Stent Coating*, http://www.sono-tek.com/biomedical/micromist_stent.html, printed Aug. 2, 2005, 3 pages.

Spagnuolo et al., *Gas 1 is induced by VE-cadherin and vascular endothelial growth factor and inhibits endothelial cell apoptosis*, Blood, vol. 103, No. 6, pp. 3005-3012 (2004).

Specialty Coating Systems, Inc., *The Parylene Press*, 4 pages (Summer 1993).

Specialty Coating Systems, Inc., *The Parylene Press*, 6 pages (Spring 1993).

Specialty Coating Systems, Inc., *The Parylene Press*, 7 pages (Winter 1992).

Specialty Coating Systems, *Parylene and Nova Tran™ Parylene Coating Services, for Unmatched Conformal Coating Performance*, 21 pages (no date).

Specialty Coating Systems, *Parylene, a Biostable Coating for Medical Applications*, 6 pages (no date).

Specialty Coating Systems, *Repair and Recoating of Parylene Coated Printed Circuit Boards*, 15 pages (no date).

Straube, *Moisture, Materials, & Buildings*, HPAC Engineering, pp. 2-7 (no date).

Taher, *Capillary interaction between a small thin solid plate and a liquid*, Mechanical and Industrial Engineering, University of Illinois at Urbana-Champaign, 4 pp. (no date).

Tamai et al., *Initial and 6-Month Results of Biodegradable Poly-I-Lactic Acid Coronary Stents in Humans*, Circulation, vol. 102, pp. 399-404 (2000).

Trident, Inc., http://www.tridentintl.com/subbody.html, printed Dec. 18, 2000, 1 page.

Trident, Inc., *Product Lines*, http://www.tridentintl.com/products-apps/ultraiet.html, printed Dec. 18, 2000, 3 pages.

Tsuji et al., *Biodegradable Polymeric Stents*, Current Interventional Cardiology Reports vol. 3, pp. 10-17 (2001).

Union Carbide Adhesion Promoters, *Union Carbide A-174 Silane*, 5 pages (Jan. 1968).

Union Carbide Electronics Division, *Parylene Environmentally Compatible Conformal Coatings for Electronic Components Assemblies and Precision Parts*, 14 pages (no date).

Union Carbide, *Abrasion Resistance of Parylene and Other Conformal Circuit Board Coatings*, Parylene Products, No. 4, 13 pages (Oct. 1977).

Union Carbide, *Adhesion Promotion Systems for Parylene*, Parylene Products, No. 15, Revision 1, 8 pages (Oct. 1977).

Union Carbide, *Adhesion Promotion Systems for Parylene*, Technology Letter, No. 15, 13 pages (Oct. 1975).

Union Carbide, *Evaluation of Parylene and Other Pellicles as Beam Splitters*, Parylene Products, No. 8, Edited, 19 pages (Oct. 1977).

Union Carbide, *Fluorescent Parylene Coatings*, Parylene Products, No. 7 Revision 1, 8 pages (Oct. 1977).

Union Carbide, *Fluorescent Parylene Coatings*, Technology Letter, No. 7, 8 pages (Oct. 1973).

Union Carbide, *Mechanical Protection Criteria for Thin Conformal Coatings*, Parylene Products, No. 3, 21 pages (Oct. 1977).

Union Carbide, *Method for Repair and Patching of Parylene Coated Printed Circuit Boards*, Parylene Products, No. 2 Revision 1, 9 pages (Oct. 1977).

Union Carbide, *Microencapsulation by Vapor Deposition*, Parylene Products, No. 6, 12 pages (Oct. 1977).

Union Carbide, *MIL I 46058, Qualification of Parylene N, C, and D*, Parylene Products, No. 1 Revision 2, 8 pages (Oct. 1977).

Union Carbide, *Parylene Bibliography*, Parylene Products, No. 5, Revision 4, 17 pages (Jan. 18, 1982).

Union Carbide, *Parylene Conformal Coatings for Hybrid Microelectronics*, Parylene Products, No. 9, 23 pages (Oct. 1973).

Union Carbide, *Parylene Pellicles for Space Applications*, Parylene Products, No. 10, 50 pages (Oct. 1977).

Union Carbide, *Parylene Pyrolysis Kinetics*, Parylene Products, No. 11, 12 pages (Oct. 1977).

Union Carbide, *Parylene Pyrolysis Kinetics*, Technology Letter, No. 11, 12 pages (May 1974).

Union Carbide, *Parylene Removal with Oxygen Plasmas*, Parylene Products, No. 18, 7 pages (Aug. 1977).

Union Carbide, *Printed Circuit Board Masking Techniques for Use with Parylene*, No. 14, Revision 1, 11 pages (Oct. 1977).

Union Carbide, *Solvent Resistance of the Parylenes*, Parylene Products, No. 12, Revision 1, 5 pages (Oct. 1977).

Union Carbide, *The Selective Removal of Parylene by Plasma Etching*, No. 13, Revision 1, 7 pages (Oct. 1977).

Union Carbide, *Thermal Endurance of the Parylenes in Air*, Parylene Products, No. 16, 4 pages (Mar. 1976).

Union Carbide, *Vapor Phase Adhesion Promotion Systems*, Parylene Products, No. 17, Revision 1, 11 pages (Oct. 1977).

van Beusekom et al., *Coronary Stent Coatings*, Coronary Artery Disease, vol. 5, No. 7, pp. 590-596 (Jul. 1994).

van der Giessen et al., *"Edge Effect" of $^{32}P$ Radioactive Stents is Caused by the Combination of Chronic Stent Injury and Radioactive Dose Falloff*, Circulation, vol. 104, pp. 2236-2241 (Oct. 30, 2001).

Vapor Inc., *Vapore-Jet™ Capillary Pump—How it Works*, http://www.vapore.com/tech_howto.htm, printed Aug. 13, 2003, 2 pages.

Völkel et al., *Targeting of immunoliposomes to endothelial cells using a single -chain Fv fragment directed against human endoglin (CD105)*, Biochemica et Biophysica Acta, vol. 1663, pp. 158-166 (Apr. 15, 2004).

von Recum et al., *Degradation of polydispersed poly(L-lactic acid) to modulate lactic acid release*, Biomaterials, vol. 16, pp. 441-445 (1995).

Welch, Van Gernert, *Optical-Thermal Response of Laser-Irradiated Tissue*, book, (1995).

Wiesendanger et al., *Contributions of Scanning Probe Microscopy and Spectroscopy to the Investigation and Fabrication of Nanometer-Scale Structures*, J. Vac. Sci. Technol. B, vol. 12, No. 2, pp. 515-529 (Mar./Apr. 1994).

Wilensky et al., *Methods and Devices for Local Drug Delivery in Coronary and Peripheral Arteries*, Trends Cardiovasc. Med., vol. 3, No. 5, pp. 163-170 (1993).

Wong et al., *An Update on Coronary Stents*, Cardio, 8 pages (Feb. 1992).

World Precision Instruments, Inc., http://www.wpiinc.com/WPI_Web/Pumps/pneumatic_Fig.gif, printed Sep. 30, 2002, 1 page.

World Precision Instruments, Inc., *Nanoliter Injector*, http://www.wpiinc.com/WPI_Web/Microinjection/Nanoliter_Injector.html, printed Jun. 10, 2005, 3 pages.

World Precision Instruments, Inc., *Nanoliter Injector*, http://www.wpi-europe.com/products/microinjection/nanoliter.htm printed Jun. 10, 2005, 2 pages.

World Precision Instruments, Inc., *Pneumatic PicoPumps*, http://www.wpieurope.com/products/microinjection/picopumps.htm, printed Jun. 10, 2005, 4 pages.

World Precision Instruments, Inc., *Pneumatic PicoPumps*, http://www.wpiinc.com/WPI_Web/Microinjection/Pneumatic_PicoPumps.html, printed Jun. 10, 2005, 4 pages.

Yau et al., *Modern Size-Exclusion Liquid Chromatography*, Wiley-Interscience Publication, 9 pages (1979).

Yoshida et al., *Modulating the phase transition temperature and thermosensitivity in N-isopropylacrylamide copolymer gels*, J. Biomat. Sci. Polymer Edn, vol. 6, No. 6, pp. 585-598 (1994).

Yokoyama et al., *Characterization of physical entrapment and chemical conjugation of adriamycin in polymeric micelles and their design for in vivo delivery to asolid tumor*, Journal of Controlled Release, vol. 50, pp. 79-92 (1998).

Yuen et al., *Tissue response to potential neuroprosthetic materials implanted subdurally*, Biomaterials, vol. 8, pp. 57-62 (Mar. 1987).

Zhmud et al., *Dynamics of Capillary Rise*, Journal of Colloid and Interface Science, vol. 228, pp. 263-269 (2000).

Zimarino et al., *Analysis of Stent Edge Restenosis with Different Forms of Brachytherapy*, The American Journal of Cardiology, vol. 89, pp. 322-325 (Feb. 1, 2002).

Zylberman et al., *Comparative Study of Electroless Co(W,P) and Co(Mo,P) Thin-Films for Capping and Barrier Layers for Cu Metallization*, 2002 Advanced Metallization Conference, 2 pages (no date).

\* cited by examiner

NANOSHELLS FOR DRUG DELIVERY

FIELD OF THE INVENTION

The present invention generally relates to chemical delivery by controlled release from an implanted device or medium. More particularly, the invention relates to composite materials containing a temperature-sensitive polymer, a drug, and light-absorbing particles, and to methods of photothermally modulating drug release.

BACKGROUND OF THE INVENTION

Modulated drug delivery allows the release profiles of therapeutic agents to be manipulated to match the physiological requirements of the patient. This type of controlled delivery system is useful for treating diseases that affect the homeostatic functions of the body, such as diabetes mellitus. Insulin therapy for diabetes requires a low baseline release of the drug, with peaks after the ingestion of food (O. B. Crofford Ann. Rev. Med. 46:267-279 (1995); F. R. Kaufmnan Pediatr. Rev. 18:383-392 (1997); and F. Ginsberg-Fellner Pediatr. Rev. 11:239-247 (1990)).

Various methods of accomplishing modulated in vivo drug delivery have been described in the literature and are currently in use or undergoing investigation. Mechanical pumps are one type of device that is commonly employed. Another method that has been examined is the use of ultrasound for rupturing tuned microcapsules or "blasting off" a layer of material from a drug-containing polymer matrix to alter drug release. That method requires use of rigid, hydrophobic polymers that are generally incompatible with proteins and other hydrophilic macromolecular drugs. Other potential problems with the routine implementation of such ultrasound techniques may exist, such as rupture of cells at high levels of insonation power, or concern about the long term safety of repetitive exposure of body tissues to ultrasonic energy.

Other methods involving sequestration of various therapeutic agents by a polymer matrix material have been examined. For example, U.S. Pat. No. 5,986,043 (Hubbell et al.) describes certain biodegradable hydrogels as carriers for biologically active materials such as hormones, enzymes, antibiotics, antineoplastic agents, and cell suspensions. Delivery of the sequestered drug depends on the in vivo degradation characteristics of the carrier.

Certain temperature sensitive hydrophilic polymer gels, or hydrogels, have been described. When the temperature of the polymer is raised above its lower critical (or consolute) solution temperature (LCST), the hydrogel undergoes a reversible phase transition that results in the collapse of the hydrogel structure (A. S. Hoffman et al. J. Contr. Rel.4:213-222 (1986); and L. C. Dong et al. J. Contr. Rel. 4:223-227 (1986)). The hydrogel collapse forces soluble materials held within the hydrogel matrix to be expelled into the surrounding solution (R. Yoshida et al. J. Biomater. Sci. Polymer Edn. 6:585-598 (1994). An impediment in the development of temperature-sensitive materials into clinically useful modulated drug delivery devices has been the lack of satisfactory means for altering the temperature of the implanted device. Ideally, the temperature change should be localized to the device to avoid damage to surrounding tissue, but the temperature change also must be rapid in order to control the conformational changes in the polymer and the drug delivery profile. Other means of altering the temperature have been proposed and are being investigated, such as heating pads, non-targeted light, RF induction heating, and exothermic chemical reactions. Other proposed techniques for controlled drug release include the application of alternating magnetic fields to certain polymers with embedded magnetic particles to effect modulation of drug delivery. Iontopheresis has also been investigated.

None of the presently available methods or devices offer a satisfactory way of obtaining localized heating to accomplish controlled, thermally actuated drug release from an implantable device while adequately avoiding potential damage to the surrounding body tissue.

The embodiments described below address the above-identified problems.

SUMMARY

The present invention provides nano-constructs for treating or ameliorating a vascular condition. The nano-constructs are gold shells formed using a self-assembled nanoconstruct. Such self-assembled nanoconstruct can be lipids, miselles or polymers. These nanoshells can comprise a gold shell and may be encapsulated inside of a liposome or polymersome. The nanoshells may also be external to the liposome or polymersome, but be bound to the surface. Alternately, the nanoshells can comprise a gold shell formed on a liposomal or polymerosome core material and optionally a bioactive agent such as a drug. To do this, the gold shell must encapsulate a dielectric (meaning non-conducting medium. See Chem. Phys. Letters 288 (1998) 243-247. A gold nanoshell encapsulating an electrically conductive core will not absorb the radiation as effectively. The nanoconstructs can be delivered to a target tissue such as a diseased tissue in a subject by any mode of delivery, e.g., injection. Upon delivery, the nano-constructs can reach the target site via passive targeting or active targeting. Energy, such as near infra-red (NIR), can then be applied to the nano-constructs. Upon exposure to energy, the nano-constructs can absorb the energy and translate the energy into heat, causing the liposomal or polymerosome core material to undergo a phase transition so as to release the bioactive agent included in the nanoshell Examples of the vascular conditions that can be treated or ameliorated by the method described herein include, but are not limited to, atherosclerotic plaque, vulnerable plaque, vascular inflammation, or diffuse atherosclerotic disease.

DETAILED DESCRIPTION

The present invention provides nano-constructs for treating or ameliorating a vascular condition. The nano-constructs are gold shells formed using a self-assembled nanoconstruct. Such self-assembled nanoconstruct can be lipids, miselles or polymers. Examples of some self-assembled nanoconstructs can be liposomal or polymerosome core material. In this case, it is preferred that the liposomal or polymersome core possess dielectric properties. Alternately, nano-constructs are gold nanoshells with a dielectric core that is encapsulated within liposomes or polymersomes. In another embodiment, the nanoconstructs consist of gold nanoshells which are conjugated or coupled to the surfaces of liposomes or polymersomes. The nano-constructs include nanoshells capable of absorbing energy from an electromagnetic radiation or energy from a fluctuating electromagnetic field and translating the energy into heat. The nanoconstructs can be delivered to a target tissue such as a diseased tissue in a subject by any mode of delivery, e.g., injection. Upon delivery, the nano-constructs can reach the target site via passive targeting or active targeting. Energy can then be applied to the nano-constructs. Upon exposure to energy, the nano-constructs can absorb the energy and translate the energy into heat, causing the liposomal or polymerosome core material to undergo a phase transition so as to release the bioactive agent included in the nanoshell. Gold nanoshells can be heated in vivo by the application of near infrared light (NIR). This allows the exploitation of naturally occurring deficit of NIR-absorbing chromaphores in most tissues, permitting transmission of 700-1000 nm light (see, Hirscch, L. R., et al., Proc Natl Acad Sci USA, 100(23):13549-13554 (2003)).

To have the gold nanoshells absorb this light, the core size and gold shell thickness can be tuned. For example, the core size can be in the range between about 55 and about 210 nm (see, e.g., Oldeburg S. J., et al., Applied Physics Letters; Vol. 75(19):2897-2899 (1999); Oldenburg S. J., et al., Chemical Physics Letters 288:243-247 (1998). The corresponding gold shell can have a thickness in the range between about 5 and about 25 nm.

In some embodiments, the nanoshell on a dielectric core can be an imperfect or porous nanoshell. When heated upon absorbing the light as described above, such imperfect nanoshells can undergo plasmon-derived optical resonance to as to cause the nanoshells to rupture, releasing an agent encapsulated/included therein.

In some embodiments, the nanoshells can comprise a gold shell formed on a liposomal core material. In other embodiments, the nanoshells comprise a gold shell encapsulating a dielectric core and the nanoshells are encapsulated within the liposome. Liposomes can have a size in the range between about 50 and about 2000 nm. For these liposomes, the gold nanoshells can be a very tight fit and could potentially occupy large amounts of the internal volume.

Alternatively, in some embodiments, gold nanoshells can be conjugated or coupled to liposomes. This can be achieved by, for example, functionalizing the liposomes with thiol groups. Such thiol groups can be provided for using a bifunctional linker that includes at least one thiol group. The linker can be first attached to the liposome to form a derivatized liposome having a thiol group. The derivatized liposome is then allowed to conjugate to or couple with gold nanoshells though the thiol group so as to form the nanoshell/liposome conjugates.

The linker can be represented by a general formula X—R—YH or (HY—R)—X—(R—YH), where X is a functional group that can be, e.g., hydroxyl, carboxyl, thiol, ketones, aldehydes, epoxides, photoreactive groups (e.g. aryl azides, benzophenone,) thiophene, amino, pyrrole, indole, phosphonic acid, hydroxyphosphonamide, or selenol; Y is NH or S; and R can be a di-radicals such as a molecular, monomeric, oligo or polymeric di-radicals. In some embodiments, R can be a short-chain alkyl group, a poly(ethylene glycol) (PEG) group, or an aryl group. In some embodiments, R can be a group derived from a polymer described below.

In some embodiments, the liposome can be functionalized with thiol group by reacting the liposome with a short, bifunctional poly(ethylene glycol) (PEG) containing N-hydroxysuccinidyl and maleimide end groups to form a derivatized phospholipid. After reacting the N-hydrosuccimidyl end, the derivatized phospholipid can be allowed to react with a large excess of a thiol agent such as dithiolthreitol to form phospholipids with thiol groups. The phospholipids with thiol groups can be allowed to couple to gold nanoshells via the reaction of thiols with gold. An alternative approach can use a difunctional PEG with thiol and carboxylic acid groups. By adjusting pH of the a solution that includes phospholipids such as a phosphatidylethanolamine phospholipids, the liposome can be selectively coupled to the carboxylic acid via DCC (dicyclohexyl-carbodiimide) chemistry so as to form derivatized liposomes with thiol groups (see, e.g.,. Ueki, T. Yanagihira; in: Peptides 1998 (Proceedings of the 25$^{th}$ European Peptide Symposium) S. Bajusz, F. Hudecz Eds; Akademiai Kiado, Budapest, 1998, p. 252; F. Albericio, et al., Tetrahedron Lett. 38:4853 (1997)). Some exemplary methods for making stealth liposomes where PEG is conjugated to ethanolamine phospholipids are described in, Kostarelos-Kostas, NATO ASI Ser, Ser A, Vol:300 (Targeting of Drugs 6), P: 139-145; J. Gittleman, et al. Polym Prepr, Vol: 38(1), p: 607; B. Ceh, et al. Adv. Drug Delivery Rev, Vol: 24 (2,3), P: 165-177; and Greg T. Hermanson, "Bioconjugate Techniques" Academic Press 1996.

By combining the thiol functional liposomes with the gold nanoshell, the liposomes can cover the surface of the gold shell via coupling with the thiol groups.

In some embodiments, the core material forming the nanoshells described herein can be large unilamellar liposomes (LUVs) encapsulating a bioactive agent such as a drug. These liposomes can have a size of about 50 to about 2000 nm. Therefore, in some embodiments, the gold nanoshells can be placed inside these large LUVs. In some embodiments, these LUVs can be modified to have thiol functional groups as described above. The gold nanoshells can be attached to the surfaces of these LUVs. Irradiation by NIR light would heat the LUVs above their sol-gel transition temperature, triggering the release of the encapsulated agent. In some embodiments, the liposomes can be small unilamellar liposomes (SUVs) encapsulating a bioactive agent such as a drug. These SUVs can have a size below about 150 nm, e.g., about 30 to about 100 nm. These SUVs can be modified to have thiol functional groups as described above. The gold nanoshells can be attached to the surfaces of these SUVs. Irradiation by NIR light would heat the SUVs above their sol-gel transition temperature, triggering the release of the encapsulated agent.

In some embodiments, the core material forming the nanoshells can be polymer vesicles (polymersomes) encapsulating a bioactive agent. In some embodiments, the core material can be hybrid vesicles including both lipid and polymer-based constituents. In some embodiments, peptide or proteins can be incorporated into the core material using DCC coupling chemistry or other coupling methodology in the art of peptide synthesis or immobilization (F. Albericio, et al., Tetrahedron Lett. 38:4853 (1997)).

In some embodiments, the core material forming the nanoshells described herein can include ferromagnetic magnetic ceramic particles.

In some embodiments, the nanoshells described herein can include targeting moieties for systemic or regional delivery. Targeting moieties for systemic or regional targeting can be incorporated either into the liposome membrane or onto the surface of the gold nanoshell. Incorporation into the liposome membrane can be achieved by coupling the targeting moiety onto a hydrophobic membrane anchor such as phospholipids. A phospholipid anchor can then be combined with liposome so as to become part of the liposome. In some embodiments, coupling of the targeting moiety can be achieved by coupling onto the gold surface of the nanoshells through thiol-terminated molecules or linkers.

The nano-constructs can be used to treat or to ameliorate a vascular condition such as atherosclerotic plaque. Other vascular conditions that can be treated or ameliorated the vascular condition include, but are not limited to, vulnerable plaque, vascular inflammation, diffuse atherosclerotic disease, or restenosis.

In some embodiments, the nanoshells include a metal or an alloy. Useful metals include gold or gold alloy. In some embodiments, the metal or metal alloy can include silver, platinum, palladium, chromium, iridium, biodegradable metals such as magnesium, zinc, calcium, or tungsten, or alloys thereof.

In some embodiments, the nanoshells include carbon. In some embodiments, the nanoshells can have a conducting polymer. Conducting polymers can be, for example, poly(pyrrole), poly(thiophene), poly(acetylene), poly(aniline), graphite, carbon nanotubes, DNA or combinations thereof.

The nanoshells have a thickness in the range between about 2 nm and about 100 nm. Thickness of the shells and the ratio of core to shell dimension is relevant to the frequency of electromagnetic radiation or irradiation that the shells can absorb and translate into heat. For example, for nanoshells formed of a metal such as gold, the wavelength at which extinction efficiency is maximal shifts to longer wavelength as core to shell ratio increases, i.e. as shell thickness decreases if the outer diameter is kept constant. Most relevant, the nanoshells can be designed such that they absorb radiation energy in the near-infrared spectrum between 650 nm and 900 nm which is permeable for tissue (see, e.g., Oldeburg S. J., et al., Applied Physics Letters; Vol. 75(19): 2897-2899; Oldenburg S. J., et al., Chemical Physics Letters 288:243-247 (1998)).

The nano-constructs described herein can be delivered to a subject for treating or ameliorating a vascular condition such as atherosclerotic plaque. Upon delivery, the nano-constructs can reach the target site via passive targeting or active targeting. Passive targeting can be achieved by extravasation of the nano-construct through leaky vasculature such as those present in atherosclerotic plaque. In some embodiments, the result of passive targeting can be assessed by the time span after delivery of the nano-constructs and the circulation time of the nano-constructs after delivery. Generally, the longer the nano-constructs remain in circulation, the more the nano-constructs can reach the target site or target tissue, which sometimes is also referred to as the diseased site or diseased tissue. Therefore, in some embodiments, passive targeting can be enhanced by increasing circulation times by rendering the surface of the nano-construct stealthy using a compound such as poly(ethylene glycol). Other compounds that can be used to stealth the nano-constructs include, but are not limited to, hyaluronic acid, phosphoryl choline, dextran, dextrose, sulfo betaine, polypyrrolidone, poly(2-hydroxyethyl methacrylate), albumin, poly(acrylic acid), and poly(methacrylic acid) and PVA.

Extravasation of the nano-constructs is also related to the position and nature of the diseased tissue. The capillary walls of tumor vasculature and the vasculature of diseased tissue is leaky compared to normal tissue. In some embodiments, extravasation can be achieved by circulation of the nano-constructs in the blood stream for a period ranging from 10 minutes to 120 hours, more specifically ranging from about 4 hours to 48 hours.

In some embodiments, the targeting can be achieved by active targeting. Active targeting can be carried out by attaching a targeting molecule on the nano-constructs (e.g., nanoshells). Targeting molecules include any peptide, antibody, or polysaccharide that has affinity to the target tissue or target site (e.g., atherosclerotic plaque). In some embodiments, the targeting molecule can be a surface-conjugated ligand against a receptor on an inflamed endothelium. Some examples of the targeting molecules are antibodies to CD34, RGD, YIGSR, peptides and antibodies to IIbIIa, heparin, hyaluronic acid, laminin, collagen, ICAM-1, ICAM-2, ICAM-3, fibrinogen, fibronectin, vitronectin, thrombospondin, osteopontin, integrins, VCAM-1, N-CAM, PECAM-1, IgCAM, folate, oligonucleotide aptamers, selectins, and cadherins.

The result of active targeting can be assessed by measuring the quantity of nano-constructs in the targeted tissue (i.e. vessel wall) versus the quantity administered. Similar to passive targeting, in some embodiments, the result of active targeting can be assessed by the time span after delivery of the nano-constructs and the circulation time of the nano-constructs after delivery. Generally, the longer the nano-constructs remain in circulation, the more the nano-constructs can reach the target site. Therefore, in some embodiments, active targeting mediated by a targeting moiety can be enhanced by increasing circulation times by stealthing the surface of the nano-construct using a compound such as poly(ethylene glycol). Other compounds that can be used to stealth the nano-constructs include, but are not limited to, hyaluronic acid, phosphoryl choline, dektran, dextrose, sulfo betaine, poly(vinyl alcohol) (PVOH), polypyrrolidone, poly(2-hydroxyethyl methacrylate), albumin, poly(acrylic acid), and poly(methacrylic acid) and PVA.

Active targeting of the nano-constructs is also related to the position and nature of the diseased tissue. Nano-constructs can reach diseased tissue, which is highly vascularized, by systemic administration. Diseased tissue protected by the blood-brain barrier, which can prevent penetration of the nano-constructs, could be more advantageously accessed by administration into cerebro-spinal fluid. If a high concentration of nano-constructs is desired in the vessel wall of a portion of the vascular system, then administration by local delivery catheter may be employed. Some target tissues such as the eye or prostate can be accessed externally by direct injection. In some embodiments, active targeting can be achieved by circulation of the nano-constructs in the blood stream for a period ranging from 10 minutes to 120 hours, more specifically ranging from about 4 hours to 48 hours.

Methods of Forming Nanoshells

Nanoshells can be formed on a core material using established methods. For example, U.S. Pat. No. 6,699,724 describes forming conducting nanoshells on a non-conducting core. The size and thickness of the core/shell can be tuned so that the particles can absorb light with a desired wavelength. Biomolecules such as proteins or peptides can be attached to the nanoshells for binding to a specific tissue.

U.S. Pat. No. 6,685,986 describes a method of forming metal nanoshells upon a core substrate. The nanoshells can be formed of a metal such as gold or a conducting polymer. The core substrate can be particles of silicon dioxide, titanium dioxide, alumina, zirconia, poly(methyl methacrylate) (PMMA), polystyrene, gold sulfide, macromolecules such as dendrimers, semiconductors such as CdSe, CdS, or GaAs. The particles can further have polyvinyl alcohol (PVA), latex, nylon, Teflon, acrylic, Kevlar, epoxy, or glasses. Some other references, for example, U.S. application publication Nos. 2003/0164064, 2002/0061363, 2002/0187347, 2002/0132045, and 2005/0056118, also describes various methods of forming metal nanoshells on a core substrate. Formation of partial nanoshells can be formed according to the method described in, for example, U.S. Pat. No. 6,660,381.

In some embodiments, the nanoshells can be formed via metal colloidal nanoparticles such as colloidal gold nanoparticles. For example, colloidal gold nanoparticles of 3-4 nm size can assemble on nanoparticle surfaces functionalized by amine groups. These nanoparticles act as nucleation sites, and when a gold salt is present in a reducing environment, a solid gold shell can be formed around a nanosize template such as a nanosphere.

In some embodiments, polymeric nanoparticles such as commercially available polystyrene particles modified at their surface to present amine groups may be used as a template for gold nanoshells. Amine functionality can be placed onto these polymers by a variety of techniques. For example, polymeric surface can be modified to have amine functionality via plasma treatment in the presence of ammonia or hydrazine. This plasma process can be carried out on preformed nanoparticles by agitating them in a plasma reactor. Amino groups can also be incorporated into the end-groups of a polymer (e.g., a biodegradable polymer), if the initiator contains both a hydroxyl group and an amino group protected by a carbobenzoxy group or a t-butoxycarbonyl group, and this initiator is used to make a biodegradable polymer by ring opening polymerization, such as poly(L-lactide) or polyglycolide. After the polymerization, the protecting group can be removed, liberating the amino group. Polymeric methacrylates can be made with amino groups by using a monomer such as N-(3-aminopropyl)methacrylamide. A copolymer with other monomers such has butyl methacrylate or methyl methacrylate can be made. In some embodiments, a dispersion or emulsion polymerization process can be used to form monodisperse nanoparticles with surface amino groups (see, e.g., Ramos; Jose, Forcada; Jacqueline. Polymer 47(4):1405 (2006); Ramos; Jose, Forcada; Jacqueline, Polymer Chemistry 43 (17):3878 (2005); Prakash, G. K. et al., J. of Nanoscience and Nanotechnology 5(3):397 (2005); and Musyanovych, Anna; Adler, Hans-Jurgen Organic Chemistry III Macromolecular Society, 21(6):2209 (2005).

In some embodiments, the nanoshells can be formed via thiol group facilitated nanoparticle assembling. For example, biodegradable poly(propylene sulfide) can be produced in nanoparticle form as shown by Annemie Rehor (Ph.D. thesis, Swiss Federal Institute of Technology, Zurich, 2005). This polymer has thiol end-groups from the polymerization, which can be maximized in number by exposing the nanoparticles to reducing conditions.

In some embodiments, the nanoshells can be modified to include a targeting molecule. The target molecule can be any peptides or antibodies such as ligands against receptors on an inflamed endothelium. Examples of such targeting molecules include, but are not limited to, antibodies to CD34, RGD, YIGSR, peptides and antibodies to IIbIIIa, heparin, hyaluronic acid, laminin, collagen, ICAM-1, ICAM-2, ICAM-3, fibrinogen, fibronectin, vitronectin, thrombospondin, osteopontin, integrins, VCAM-1, N-CAM, PECAM-1, IgCAM, folate, oligonucleotide aptamers, selectins, and cadherins.

Attachment of targeting molecule to nanoshells can be achieved by established methods. The targeting molecule can be attached to the nanoshell via covalent bonding or non-covalent conjugation. Non-covalent conjugation can be based on ionic interaction, hydrogen bonding or other type of interaction. For example, after formation of the gold nanoshell, molecules functionalized with a thiol group can be used to modify the nanoshell surface for targeting of the nanoshell, or to stealth the nanoshell surface. Thiol-terminated molecules have been shown to self-assemble on gold surfaces. For example, thiol-terminated poly(ethylene glycol) (PEG) having a molecular weight of about 200 Daltons to 10,000 Daltons, preferably between 500 Daltons to about 2,000 Daltons can be used to stealth the nanoshell surface. The other end of the PEG chain can be functionalized with a targeting molecule such as a peptide or an antibody to target the nanoshell to specific tissue within the body.

In some embodiments, the targeting molecule can be attached to a nanoshell via a spacer. A spacer molecule can be a short chain alkyl group such as a C1-C20 alkyl, C3-C20 cycloalkyl, poly(ethylene glycol), poly(alkylene oxide). Some other spacer molecules can be, but are not limited to, dextran, dextrose, heparin, poly(propylene sulfide), hyluronic acid, peptides, DNA, PVA and PVP.

Bioactive Agents

The medical device that can be delivered using the nanoshells described herein can include one or more bioactive agent(s), which can be therapeutic, prophylactic, or diagnostic agent(s). These agents can have anti-proliferative or anti-inflammatory properties or can have other properties such as antineoplastic, antiplatelet, anti-coagulant, anti-fibrin, antithrombogenic, antimitotic, antibiotic, antiallergic, antifibrotic, and antioxidant. The agents can be cystostatic agents, agents that promote the healing of the endothelium such as NO releasing or generating agents, agents that attract endothelial progenitor cells, agents that promote the attachment, migration and proliferation of endothelial cells (e.g., natriuretic peptides such as CNP, ANP or BNP peptide or an RGD or cRGD peptide), while impeding smooth muscle cell proliferation. Examples of suitable therapeutic and prophylactic agents include synthetic inorganic and organic compounds, proteins and peptides, polysaccharides and other sugars, lipids, and DNA and RNA nucleic acid sequences having therapeutic, prophylactic or diagnostic activities. Some other examples of the bioactive agent include antibodies, receptor ligands, enzymes, adhesion peptides, blood clotting factors, inhibitors or clot dissolving agents such as streptokinase and tissue plasminogen activator, antigens for immunization, hormones and growth factors, oligonucleotides such as antisense oligonucleotides, small interfering RNA (siRNA), small hairpin RNA (shRNA), aptamers, ribozymes and retroviral vectors for use in gene therapy. Examples of anti-proliferative agents include rapamycin and its functional or structural derivatives, 40-O-(2-hydroxy)ethyl-rapamycin (everolimus), and its functional or structural derivatives, paclitaxel and its functional and structural derivatives. Examples of rapamycin derivatives include 40-epi-(N1-tetrazolyl)-rapamycin (ABT-578), 40-O-(3-hydroxy)propyl-rapamycin, 40-O-[2-(2-hydroxy)ethoxy]ethyl-rapamycin, and 40-O-tetrazole-rapamycin. Examples of paclitaxel derivatives include docetaxel. Examples of antineoplastics and/or antimitotics include methotrexate, azathioprine, vincristine, vinblastine, fluorouracil, doxorubicin hydrochloride (e.g. Adriamycin® from Pharmacia & Upjohn, Peapack N.J.), and mitomycin (e.g. Mutamycin® from Bristol-Myers Squibb Co., Stamford, Conn.). Examples of such antiplatelets, anticoagulants, antifibrin, and antithrombins include sodium heparin, low molecular weight heparins, heparinoids, hirudin, argatroban, forskolin, vapiprost, prostacyclin and prostacyclin analogues, dextran, D-phe-pro-arg-chloromethylketone (synthetic antithrombin), dipyridamole, glycoprotein IIb/IIIa platelet membrane receptor antagonist antibody, recombinant hirudin, thrombin inhibitors such as Angiomax (Biogen, Inc., Cambridge, Mass.), calcium channel blockers (such as nifedipine), colchicine, fibroblast growth factor (FGF) antagonists, fish oil (omega 3-fatty acid), histamine antagonists, lovastatin (an inhibitor of HMG-CoA reductase, a cholesterol lowering drug, brand name Mevacor® from Merck & Co., Inc., Whitehouse Station, N.J.), monoclonal antibodies (such as those specific for Platelet- Derived Growth Factor (PDGF) receptors), nitroprusside, phosphodiesterase inhibitors, prostaglandin inhibitors, suramin, serotonin blockers, steroids, thioprotease inhibitors, triazolopyrimidine (a PDGF antagonist), nitric oxide or nitric oxide donors, super oxide dismutases, super oxide dismutase mimetic, 4-amino-2,2,6,6-tetramethylpiperidine-1-oxyl (4-amino-TEMPO), estradiol, anticancer agents, dietary supplements such as various vitamins, and a combination thereof. Examples of anti-inflammatory agents including steroidal and non-steroidal anti-inflammatory agents include tacrolimus, dexamethasone, clobetasol, or combinations thereof. Examples of cytostatic substances include angiopeptin, angiotensin converting enzyme inhibitors such as captopril (e.g. Capoten® and Capozide® from Bristol-Myers Squibb Co., Stamford, Conn.), cilazapril or lisinopril (e.g. Prinivil® and Prinzide® from Merck & Co., Inc., Whitehouse Station, N.J.). An example of an antiallergic agent is permirolast potassium. Other therapeutic substances or agents which may be appropriate include alpha-interferon, pimecrolimus, imatinib mesylate, midostaurin, bioactive RGD, SIKVAV peptides, elevating agents such as cANP or cGMP peptides, and genetically engineered endothelial cells. The foregoing substances can also be used in the form of prodrugs or co-drugs thereof. The foregoing substances also include metabolites thereof and/or prodrugs of the metabolites. The foregoing substances are listed by way of example and are not meant to be limiting. Other active agents which are currently available or that may be developed in the future are equally applicable.

The dosage or concentration of the bioactive agent required to produce a favorable therapeutic effect should be less than the level at which the bioactive agent produces toxic effects and greater than non-therapeutic levels. The dosage or concentration of the bioactive agent can depend upon factors such as the particular circumstances of the patient, the nature of the trauma, the nature of the therapy desired, the time over which the administered ingredient resides at the vascular site, and if other active agents are employed, the nature and type of the substance or combination of substances. Therapeutically effective dosages can be determined empirically, for example by infusing vessels from suitable animal model systems and using immunohistochemical, fluorescent or electron microscopy methods to detect the agent and its effects, or by conducting suitable in vitro studies. Standard pharmacological test procedures to determine dosages are understood by one of ordinary skill in the art.

Method of Use

The nano-constructs provided herein can be delivered or administered to a subject via any established mode of delivery. For example, the nano-constructs can be delivered by systemic delivery such as systemic injection. In some embodiments, the nano-constructs can be administered by local delivery such as direct injection. For disorders of the vascular system, the nano-constructs may be administered by catheter-based devices. These would include single and dual needle injection catheters, porous balloon catheters, balloon catheters with jets, and double balloon catheters.

Upon delivery to the target tissue, an energy source can be applied to the nano-constructs. The nano-constructs can then absorb the energy and convert it or translate it to heat so as to cause the liposomal structure in the nano-construct to collapse to release a bioactive agent included in the nano-construct. The energy source can be in any form capable of reaching the nano-constructs and being absorbed and converted by the nano-constructs into heat. In some embodiments, the energy source can be applied through external radiation or through a catheter-based guidance system.

In some embodiments, the energy source is an electromagnetic radiation having a wave length ranging from 500 nm to 1500 nm. For example, the energy source can be a near infrared radiation.

In some embodiments, the energy source is a fluctuating electromagnetic field. Such electromagnetic field can have a frequency ranging from $1 \times 10^6$ Hz to $6 \times 10^{14}$ Hz. In some embodiments, the electromagnetic field can have a frequency of 700 nm to 1300 nm where optical transmission is optimal (Welch A.; van Gemert, M. e. *Optical-Thermal Response of Laser Irradiated Tissue*, Plenum Press: New York, 1995).

In some embodiments, the energy source is applied to the nano-constructs by a catheter-based fiber-optic. The localization of plaque can be imaged prior to the procedure or during the procedure by interrogation with an attenuated radiation. For example, the plaque may be imaged by optical coherence tomography using a wavelength of 1300 nm (Meissner O. A., et al. J Vasc Interv Radiol 2006; 17: 343-349) or intravascular ultrasound (Colombo et al., Circulation, 91:1676-88 (1995)). This same wavelength could then be used to apply energy to the nano-constructs after they are administered.

The nano-construct described herein can be used to target and deliver a bioactive agent at a site of medical condition where delivery of the bioactive agent is desirable for treating, preventing or ameliorating the medical condition. Such a medical condition can be, e.g., a tumor or nephropathic kidney. In some embodiments, such a site can be a site of atherosclerosis. Other medical conditions include, but are not limited to, vulnerable plaque, diffuse atherosclerotic disease, diabetic retinopathy, aneurysm, anastomotic hyperplasia, claudication, chronic total occlusion, dysfunctional endothelium, recurring thrombus, fibrin accumulation, or combinations of these.

While particular embodiments of the present invention have been shown and described, it will be apparent to those skilled in the art that changes and modifications can be made without departing from this invention in its broader aspects. Therefore, the appended claims are to encompass within their scope all such changes and modifications as fall within the true spirit and scope of this invention.

We claim:

1. A nano-construct comprising
    (a) a metal or metal alloy nanoshell formed around a core material, and
    (b) a bioactive agent,
    wherein the core material comprises a material selected from the group consisting of a liposome, a polymersome, and a hybrid vesicle comprising both lipid and polymer-based constituents,
    wherein the core material further comprises dielectric material, which comprises magnetic ceramic particles.

2. The nano-construct of claim 1, wherein the nanoshell is a gold nanoshell.

3. The nano-construct of claim 1, comprising a large unilamellar vesicle,
    wherein the large unilamellar vesicle encapsulates the nanoshell and the bioactive agent.

4. The nano-construct of claim 1, wherein the core material is a small unilamellar vesicle encapsulating the bioactive agent.

5. The nano-construct of claim 1, wherein the nanoshell is a gold nanoshell having a thickness in the range between about 5 and about 25 nm.

6. The nano-construct of claim 1, wherein the core material is a liposome having a size in the range between about 150 nm to about 200 nm.

7. The nano-construct of claim 1, wherein the metal or metal alloy nanoshell surrounding the core is porous to the bioactive agent once it is released from the core material.

8. The nano-construct of claim 2, wherein the gold nanoshell surrounds the core of a dielectric material, and
wherein a plurality of these gold shells are conjugated to the surface of the core material, which contains the bioactive agent.

9. The nano-construct of claim 1, wherein the core material comprises a peptide, a protein, or a combination of these.

10. The nano-construct of claim 1, further comprising a targeting molecule on the surface of the nano-construct.

11. The nano-construct of claim 10, wherein the targeting molecule is a surface-conjugated ligand against one or more receptors on an inflamed endothelium.

12. The nano-construct of claim 1 in a formulation suitable for systemic delivery or local delivery into a human being.

13. The nano-construct of claim 12, wherein the systemic delivery is injection.

14. The nano-construct of claim 12, wherein the local delivery is delivery by a device comprising a catheter.

15. The nano-construct of claim 1, wherein the bioactive agent is paclitaxel, docetaxel, estradiol, 17-beta-estradiol, nitric oxide donors, super oxide dismutases, super oxide dismutases mimics, 4-amino-2,2,6,6-tetramethylpiperidine-1-oxyl, tacrolimus, dexamethasone, rapamycin, 40-O-(2-hydroxy)ethyl-rapamycin, 40-O-(3-hydroxy)propyl-rapamycin, 40-O-[2-(2-hydroxy)ethoxy]ethyl-rapamycin, 40-O-tetrazole-rapamycin, 40-epi-(N1-tetrazolyl)-rapamycin, γ-hirudin, clobetasol, pimecrolimus, imatinib mesylate, or midostaurin, or prodrugs, or combinations of these.

16. A method of forming a nano-construct according to claim 1, comprising:
providing a core material selected from a liposome, a polymerosome, a hybrid vesicle,
forming a nanoshell around the core material.

17. The method of claim 16, wherein the core material encapsulates a bioactive agent.

18. The method of claim 16, wherein the formed nanoshell has porosity.

19. The method of claim 16, wherein the core material is a liposome.

20. The method of claim 16, wherein the nanoshell is a gold nanoshell having a thickness in the range between about 5 and about 25 nm.

21. The method of claim 16, wherein the liposome has a size in the range between about 150 nm to about 200 nm.

22. The method of claim 16, wherein the core material comprises a peptide, a protein, or a combination of these.

23. The method of claim 16, wherein the nano-construct comprises a targeting molecule on the surface of the nano-construct.

24. The method of claim 23, wherein the targeting molecule is a suface-conjugated ligand against receptors on an inflamed endothelium.

25. The method of claim 16, wherein the nano-construct is in a formulation suitable for systemic delivery or local delivery into a human being.

26. The method of claim 25, wherein the systemic delivery is injection.

27. The method of claim 25, wherein the local delivery is delivery by a device comprising a catheter.

28. The method of claim 16, wherein the bioactive agent is paclitaxel, docetaxel, estradiol, 17-beta-estradiol, nitric oxide donors, super oxide dismutases, super oxide dismutases mimics, 4-amino-2,2,6,6-tetramethylpiperidine-1-oxyl, tacrolimus, dexamethasone, rapamycin, rapamycin derivatives, 40-O-(2-hydroxy)ethyl-rapamycin, 40-O-(3-hydroxy)propyl-rapamycin, 40-O-[2-(2-hydroxy)ethoxy]ethyl-rapamycin, 40-O-tetrazole-rapamycin, 40-epi-(N1-tetrazolyl)-rapamycin, γ-hirudin, clobetasol, pimecrolimus, imatinib mesylate, or midostaurin, or prodrugs, or combinations of these.

* * * * *